US010168549B2

(12) United States Patent
Ohlendorf et al.

(10) Patent No.: US 10,168,549 B2
(45) Date of Patent: Jan. 1, 2019

(54) OPTICAL VISUAL AID WITH ADDITIONAL ASTIGMATISM

(71) Applicant: Carl Zeiss Vision International GmbH, Aalen (DE)

(72) Inventors: Arne Ohlendorf, Aalen (DE); Rainer Sessner, Roth (DE); Timo Kratzer, Aalen (DE); Katharina Rifai, Tübingen (DE); Christian Lappe, Mutlangen (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 15/594,338

(22) Filed: May 12, 2017

(65) Prior Publication Data

US 2017/0261767 A1    Sep. 14, 2017

Related U.S. Application Data

(63) Continuation-in-part of application No. PCT/EP2015/076344, filed on Nov. 11, 2015.

(30) Foreign Application Priority Data

Nov. 14, 2014  (DE) .................. 10 2014 223 341
Apr. 10, 2015  (AT) .................. 50281/2015

(51) Int. Cl.
*A61B 3/02*   (2006.01)
*G02C 7/02*   (2006.01)
(Continued)

(52) U.S. Cl.
CPC ............. *G02C 7/081* (2013.01); *A61B 3/02* (2013.01); *G02C 7/02* (2013.01); *G02C 7/024* (2013.01); *G02C 7/06* (2013.01)

(58) Field of Classification Search
USPC ........................................... 351/239
See application file for complete search history.

(56) References Cited

U.S. PATENT DOCUMENTS 5,557,348 A   9/1996 Umeda et al.
6,089,713 A   7/2000 Hof et al.
(Continued)

FOREIGN PATENT DOCUMENTS

DE   102007032001 A1   1/2009
DE   102012014399 A1   5/2014
(Continued)

OTHER PUBLICATIONS

M. R. Sawusch et al.: "Optimal Astigmatism to Enhance Depth of Focus after Cataract Surgery," Ophthalmology, vol. 98, pp. 1025 to 1029, 1991.
(Continued)

Primary Examiner — Zachary W Wilkes
(74) Attorney, Agent, or Firm — Ewers & Hasselmann PLLC

(57) ABSTRACT

An optical visual aid is disclosed that assists an observer looking at an object through at least one spectacle lens. The optical visual aid has a dioptric power matched to an eye of the observer for at least one viewing direction. The dioptric power is composed of a plurality of dioptric power components. A first dioptric power component of the plurality of dioptric power components has a best possible corrective power for the eye of the observer at a defined distance of the object from the corneal vertex of the eye for the viewing direction. At the same time, a further dioptric power component of the plurality of dioptric power components has an additional astigmatic, partly corrective power for the viewing direction for the eye of the observer at the defined distance.

17 Claims, 9 Drawing Sheets

(51) Int. Cl.
*G02C 7/06* (2006.01)
*G02C 7/08* (2006.01)

(56) References Cited

U.S. PATENT DOCUMENTS

| | | | |
|---|---|---|---|
| 6,318,859 | B1 | 11/2001 | Baudart et al. |
| 7,108,373 | B2 * | 9/2006 | Yamakaji ................. G02C 7/02 351/159.74 |
| 7,537,343 | B2 | 5/2009 | Kanazawa et al. |
| 7,744,217 | B2 | 6/2010 | Cabeza et al. |
| 2009/0210054 | A1 | 8/2009 | Weeber et al. |
| 2011/0116037 | A1 | 5/2011 | Gupta et al. |
| 2011/0279912 | A1 | 11/2011 | Fiala |
| 2013/0321762 | A1 | 5/2013 | Weeber et al. |
| 2013/0060330 | A1 | 7/2013 | Gupta et al. |
| 2015/0134473 | A1 | 5/2015 | Saur et al. |

FOREIGN PATENT DOCUMENTS

| | | |
|---|---|---|
| EP | 0632308 A1 | 1/1995 |
| EP | 0857993 A2 | 8/1998 |
| EP | 0927377 B1 | 7/2002 |
| EP | 1880663 A1 | 1/2008 |
| WO | 03/009746 A1 | 2/2003 |
| WO | 2010/065475 A2 | 6/2010 |
| WO | 2010/083546 A2 | 7/2010 |
| WO | 2012/046230 A1 | 4/2012 |

OTHER PUBLICATIONS

G.M. Spitzlberger: "Änderung der optischen Aberrationen des menschlichen Auges durch Laser in situ Keratomileusis [Change in the optical aberrations of the human eye by laser in-situ keratomileusis]," dissertation 2004 and machine translation of abstract.

International Search Report of the European Patent Office in PCT/EP2015/076344 (from which this application claims priority) dated Feb. 9, 2016 and English-language translation thereof.

International Preliminary Report of Patentability of the European Patent Office in PCT/EP2015/076344 (from which this application claims priority) dated Feb. 23, 2017.

International Preliminary Report of Patentability of the European Patent Office in PCT/EP2015/076344 (from which this application claims priority) dated May 18, 2017.

Office action of the Australian Patent Office dated Jan. 3, 2018 and amended specification of Australian Patent application 2015345119, which is a counterpart application of this application.

Office action of the Canadian Patent Office dated Jan. 19, 2018 and Response to Examination Report submitted Dec. 29, 2017 in Canadian Patent application 2967715, which is a counterpart application of this application.

* cited by examiner

OPTICAL VISUAL AID WITH ADDITIONAL ASTIGMATISM

CROSS REFERENCE TO RELATED APPLICATIONS

This application is a continuation-in-part application of International Application No. PCT/EP2015/076344 filed on Nov. 11, 2015, and claims priority to German patent application DE 10 2014 223 341.0 filed on Nov. 14, 2014, and to Austrian patent application A 50281/2015 filed on Apr. 10, 2015, all of which are hereby incorporated by reference in their entireties as if fully set forth herein.

TECHNICAL FIELD

The disclosure relates to the calculation or manufacture or selection of an optical visual aid comprising at least one spectacle lens to be used by an observer for looking at an object, wherein the optical visual aid has a dioptric power matched to an eye of the observer for at least one viewing direction, the dioptric power being composed of a plurality of dioptric power components. Moreover, the disclosure also relates to a method for ascertaining a parameterization of the dioptric power, composed of a plurality of dioptric power components, of an optical visual aid for an eye of an observer, which has a dioptric power matched to the eye of the observer. Moreover, the disclosure relates to a computer program for carrying out the method and a system for providing or manufacturing an optical visual aid with at least one spectacle lens for use by an observer for looking at an object, in which a sought parameterization of the dioptric power, composed from a plurality of dioptric power components, of an optical visual aid may be ascertained.

BACKGROUND

An optical visual aid is understood by this disclosure to mean, in particular, spectacles with a spectacle lens which is positionable in front of the eye of an observer. However, an optical visual aid within the meaning of the disclosure is also any arrangement of optical elements, positionable in front of the eye of an observer, having at least one spectacle lens or a plurality of spectacle lenses with different optical properties.

A dioptric power component of the dioptric power of the visual aid is understood by this disclosure to mean a contribution of the visual aid in the form of at least spherical power (sphere) and astigmatic power (cylinder and associated axis location) for compensating the refractive error of the observer.

Below, the spherical power (spherical refractive power) of an optical element is specified using the unit $[D]=[1/m]$ (diopter); the astigmatic power (cylindrical refractive power) of an optical element is specified using the unit $[DC]=[1/m]$ and the axis location in degrees.

Within the meaning of the disclosure, a best possible corrective power of a dioptric power component of the dioptric power of the visual aid is understood to mean the property of the dioptric power component that the contribution of the dioptric power component to the dioptric power of the visual aid overall compensates the so-called habitual refraction deficit of the observer at least to $\frac{1}{8}$ D, preferably to $\frac{1}{8}$ D, of the spherical power, at least to $\frac{1}{8}$ DC, preferably to $\frac{1}{8}$ DC, of the astigmatic power, and $\pm 5°$ axis location. The habitual refraction deficit may be ascertained by, e.g., a refraction.

In general, the optician or ophthalmologist creates a prescription with prescription values for a best possible corrective power of the aforementioned dioptric power component of the visual aid.

The partly corrective power of a dioptric power component of the dioptric power of the visual aid is understood by this disclosure to mean the property of this dioptric power component that the contribution of the dioptric power component to the dioptric power of the visual aid overall at least partly corrects the so-called habitual refraction deficit of the observer. A dioptric power component is only partly corrective within the meaning of the disclosure if, on account of the merely partly corrective power, the visual acuity of the observer has been reduced by no more than 0.2 log MAR (Logarithm of the Minimum Angle of Resolution) in relation to the visual acuity obtained by a dioptric power component having a best possible corrective power within the meaning of the disclosure.

The disclosure combines one or more dioptric power components for a best possible corrective power and one or more dioptric power components for a partly corrective power. Here, the partly corrective power may be realized by combining different optical elements in a visual aid or by a single optical element, e.g., a spectacle lens with a dioptric power which is composed of dioptric power components with a spherical power and/or an astigmatic power and/or a prismatic power.

So that an observer is able to see an object arranged in a certain distance region in focus, the object needs to be imaged in focus on the retina of the eyes of the observer. A precondition for this is either that the image produced on the retina lies exactly in an image plane conjugate to the object plane or that the depth-of-field of the image of the object is so large that the unsharpness connected with an imaging on the retina from the image plane conjugate to the object plane cannot be perceived by the observer.

The visual faculty of the human eye is also referred to as visual acuity V. The visual acuity of the human eye is defined as the visual angle, measured in arc minutes, at which an observer is just still able to identify an object with the eye under an aperture angle $\alpha$ of the observation pencil of rays:

$$V:=\alpha/1'$$

Thus, the eye of an observer with a visual acuity of 1 is just still able to resolve a 1.5 mm large object at a distance of 5 m.

So-called eyesight test devices are used for checking the visual acuity, such as the i.Polatest® eyesight test device or the Visuscreen 500 eyesight test device, both made by Zeiss. Using this eyesight test device, different optotypes in the form of signs embodied as a Landolt ring or as a tumbling E or as numbers or letters with different sizes may be visualized for the eyes of an observer by way of projection onto a display area. U.S. Pat. No. 7,537,343 describes an eyesight test device with a display for displaying optotypes. The different dimensions of the optotypes, which are shown to an observer in the eyesight test devices, in this case correspond to different values of the visual acuity. To test the visual acuity, the optotypes displayed to an observer are reduced in size until the observer can no longer clearly identify the optotypes, but can only still guess these.

The healthy human eye is capable of ensuring sharp imaging on the retina by changing the form of the natural lens of the eye for objects that lie in different distance regions. This ability is referred to as the so-called accommodation capability. With increasing age, the human eye loses the ability of clearly identifying small objects at a short object distance. This is due to the accommodation capability of the human eye reducing with increasing age and hence the eye becomes ametropic for objects lying in the vicinity (presbyopia).

Refractive errors of the human eyes may often be corrected completely, or at least in part, by means of optical visual aids.

The use of an optical visual aid of the type set forth at the outset is known from U.S. Pat. No. 6,089,713. Described therein is a spectacle lens embodied as a progressive addition lens, which has a dioptric power matched to the eye of an observer. Here, this dioptric power of the spectacle lens is composed of a plurality of dioptric power components which belong to different visual zones of the progressive addition lens. This facilitates in-focus vision in different distance regions for an observer, even in the case of a restricted accommodation capability.

US 2009/0210054 A1 describes an optical visual aid with a spectacle lens which has an astigmatism for increasing the depth of field. U.S. Pat. No. 5,557,348, US 2011/0116037 A1, and US 2011/0279912 also disclose such spectacle lenses.

The article "Optimal Astigmatism to Enhance Depth of Focus after Cataract Surgery," Ophthalmology 98, 1025 (1991) to Sawusch M. R. et al. proposes to provide a positive astigmatism corresponding to the spherical refractive power in intraocular lenses, according to the following relationship:

plus cylinder=−sphere−0.25.

SUMMARY

It is an object of the disclosure to allow an observer to observe objects with an increased depth of field and to specify a method and a system for ascertaining a parameterization of an optical visual aid, by which an observer may observe objects with an increased depth of field.

The spectacle lens of an optical visual aid used according to the disclosure may, for example, be embodied as a multifocal lens, in particular as a progressive addition lens. The spectacle lens of an optical visual aid used according to the disclosure may also have a prescription surface. By way of example, this prescription surface may be a spectacle lens rear surface.

A visual aid used according to the disclosure has, for at least one viewing direction, a dioptric power matched to an eye of the observer, the dioptric power being composed of a plurality of dioptric power components. Here, a first dioptric power component of the plurality of dioptric power components has a best possible corrective power for the viewing direction for the eye of the observer in a defined distance region. A further dioptric power component of the plurality of dioptric power components has an additional astigmatic, partly corrective power for the viewing direction for the eye of the observer in the defined distance region. Expressed differently, the visual aid provided for the spectacles wearer does not have precisely the prescription values, ascertained according to a conventional spectacle prescription on account of a determination of the refraction, for the spherical power, the astigmatic power and the axis location thereof and, optionally, for the prismatic power and the basis thereof, which provide a best possible corrective power for a viewing direction, but it has an additional astigmatic power with an axis location possibly deviating from the axis location according to the spectacle prescription or with a corresponding axis location for a partly corrective power.

This is because the inventors have recognized that the natural depth of field of the human eye may be increased using an optical visual aid having an additional astigmatic power. Thus, an astigmatism is induced for the eye of the observer using an optical visual aid in accordance with the disclosure.

In the present case, the use of a visual aid should be understood to mean, in particular, that the visual aid which provides the dioptric power for the observer specified above, is selected from stock present in virtual or physical form. Alternatively, a visual aid may naturally also be calculated and manufactured individually for the observer. Furthermore, this may be referred to, here, as prescription manufacturing, with the data underlying the manufacturing—as described above—not being precisely the prescription values determined from a refraction measurement, but instead the data being modified by the above-described additional astigmatic power with the associated axis location for a partly corrective power.

Against this backdrop, the inventors found, in particular, that the natural depth of field of the human eye may be optimized if the first power component has a power which, for the distance, corrects the eye of the observer to the best possible extent and the second power component, which differs from the first power component, has an additional negative astigmatic power for the eye of the observer.

In particular, the inventors found out that, if the first power component has a power which, for a distance $A_S \geq 4$ m of an object from the corneal vertex of the eye, corrects the eye of the observer to the best possible extent for the viewing direction and the further dioptric power component has an additional negative astigmatic power for the eye of the observer for the viewing direction, a particularly good visual impression may be obtained by virtue of the additional negative astigmatic power being a cylindrical refractive power BK, with the following applying to the cylindrical refractive power BK: $-1.0$ DC$\leq$BK$\leq-0.125$ DC, preferably $-0.7$ DC$\leq$BK$\leq-0.3$ DC, particularly preferably BK$\approx-0.5$ DC, and wherein the additional negative astigmatic power has an axis location $\varphi$, specified in the TABO (Technischer Ausschuß für BrillenOptik) scheme, with $70°\leq\varphi\leq110°$, preferably $80°\leq\varphi\leq100°$, particularly preferably $\varphi\approx90°$, or an axis location $\varphi$, specified in the TABO scheme, with an axis location $\varphi$, specified in the TABO scheme, with $-20°\leq\varphi\leq20°$, preferably $-10°\leq\varphi\leq10°$, particularly preferably $\varphi\approx0°$.

A particularly good visual impression may also be obtained by virtue of the fact that the first dioptric power component has a power which, for a distance $A_S \leq 1$ m of an object from the corneal vertex of the eye, corrects the eye of the observer to the best possible extent for the viewing direction and the further dioptric power component has an additional negative astigmatic power for the eye of the observer for the viewing direction, wherein the additional negative astigmatic power has a cylindrical refractive power BK with $-1.0$ DC$\leq$BK$\leq-0.125$ DC, preferably $-0.7$ DC$\leq$BK$\leq-0.3$ DC, particularly preferably BK$\approx-0.5$ DC and an axis location $\varphi$, specified in the TABO scheme, with $70°\leq\varphi\leq110°$, preferably $80°\leq\varphi\leq100°$, particularly preferably $\varphi\approx90°$.

The inventors moreover found out that a good visual impression may be obtained by virtue of the fact that the first dioptric power component has a power which, for a distance AS$\leq$1 m of an object from the corneal vertex of the eye, corrects the eye of the observer to the best possible extent for the viewing direction and the further dioptric power component has an additional negative astigmatic power for the eye of the observer for the viewing direction, wherein the additional negative astigmatic power has a cylindrical refractive power BK with $-1.0$ DC≤BK≤$-0.125$ DC, preferably $-0.7$ DC≤BK≤$-0.3$ DC, particularly preferably BK≈$-0.5$ DC and an axis location φ, specified in the TABO scheme, with $-20°≤φ≤20°$, preferably $-10°≤φ≤10°$, particularly preferably φ≈0°. This is because the inventors determined that this astigmatism specified above does not have a disadvantageous effect on the depth of field perceived by an observer.

The inventors have identified that the addition in progressive addition lenses may be reduced if these lenses have an additional astigmatism with the above-specified power in the near region zone, with this additional astigmatism increasing the depth of field, with the accommodation-assisting power remaining the same.

Therefore, it is also an idea of the disclosure that, in the optical visual aid, the first dioptric power component has a spherical refractive power SBK for the viewing direction which has been reduced by the value ΔSBK, with $-1.0$ D≤ΔSBK≤$-0.1$ D, in relation to a power which, for a distance 25 cm≤$A_S$≤40 cm, preferably $A_S$≈33 cm, of an object from the corneal vertex of the eye, corrects the eye of the observer to the best possible extent.

In an optical visual aid according to the disclosure, the dioptric power matched to the eye of the observer may also be composed of at least two first and two further dioptric power components. One of the two first dioptric power components then has a power which, for a distance $A_S$≤1 m of an object from the corneal vertex of the eye, corrects the eye of the observer to the best possible extent for the viewing direction. The other one of the two first dioptric power components has a power which, for a distance $A_S$≥4 m of the object from the corneal vertex of the eye, corrects the eye of the observer to the best possible extent for a further viewing direction. Here, one of the two second dioptric power components has an additional negative astigmatic, partly corrective power for the eye of the observer with a cylindrical refractive power BK with $-1.0$ DC≤BK≤$-0.125$ DC, preferably $-0.7$ DC≤BK≤$-0.3$ DC, particularly preferably BK≈$-0.5$ DC, and an axis location φ, specified in the TABO scheme, with $70°≤φ≤110°$, preferably $80°≤φ≤100°$, particularly preferably φ≈90° for the viewing direction.

However, it should be noted that, in the case of an optical visual aid according to the disclosure, provision may also be made for the dioptric power matched to the eye of the observer to be composed of at least two first and two further dioptric power components, wherein one of the two first dioptric power components has a power which, for a distance $A_S$≤1 m of an object from the corneal vertex of the eye, corrects the eye of the observer to the best possible extent for the viewing direction and the other one of the two first dioptric power components has a power which, for a distance $A_S$≥4 m of the object from the corneal vertex of the eye, corrects the eye of the observer to the best possible extent for a further viewing direction and wherein, in this case, one of the two second dioptric power components has an additional negative astigmatic, partly corrective power for the eye of the observer with a cylindrical refractive power BK with $-1.0$ DC≤BK≤$-0.125$ DC, preferably $-0.7$ DC≤BK≤$-0.3$ DC, particularly preferably BK≈$-0.5$ DC, and an axis location φ, specified in the TABO scheme, with $-20°≤φ≤20°$, preferably $-10°≤φ≤10°$, particularly preferably φ≈0°, for the viewing direction.

The other one of the two second dioptric power components of an optical visual aid specified above then has an additional negative astigmatic power for the eye of the observer with a cylindrical refractive power BK with $-1.0$ DC≤BK≤$-0.125$ DC, preferably $-0.7$ DC≤BK≤$-0.3$ DC, particularly preferably BK≈$-0.5$ DC, and with an axis location φ, specified in the TABO scheme, with $70°≤φ≤110°$, preferably $80°≤φ≤100°$, particularly preferably φ≈90° for the further viewing direction or with an axis location φ with $-20°≤φ≤20°$, preferably $-10°≤φ≤10°$, particularly preferably φ≈0° for the further viewing direction.

To ascertain the parameterization sought for an observer of the dioptric power of the optical visual aid composed of a plurality of dioptric power components, the disclosure proposes, as a method, that a first parameterization of the optical visual aid is determined for at least one defined distance $A_S$ of an object from the corneal vertex of the eye for a viewing direction from a best possible correction of the eye of the observer. Then, the ascertained first parameterization is corrected by an additional dioptric power component and the correspondingly corrected first parameterization is thereupon set as the sought parameterization.

By way of example, the first parameterization may be the determination of the prescription values for the spherical power, the astigmatic power and the axis location thereof and, optionally, for the prismatic power and the basis thereof from a subjective and/or objective refraction measurement. In the case of a presbyopic person, the refraction measurement may comprise not only a refraction measurement for the person looking into the distance (far-point refraction), but also, or alternatively, one or more refraction measurements in different viewing directions and/or at different object distances.

Here, preferably, the best possible correction for the eye of the observer is a best possible correction for a distance $A_S$≤1 m of an object from the corneal vertex of the eye for the viewing direction, wherein the additional dioptric power component has an additional negative astigmatic power for the eye of the observer and wherein the additional negative astigmatic power is a cylindrical refractive power BK with $-1.0$ DC≤BK≤$-0.125$ DC, preferably $-0.7$ DC≤BK≤$-0.3$ DC, particularly preferably BK≈$-0.5$ DC and with an axis location φ, specified in the TABO scheme, with $70°≤φ≤110°$, preferably $80°≤φ≤100°$, particularly preferably φ≈90°.

However, the inventors have also determined that the depth of field perceived by the observer does not noticeably deteriorate in the case where a correction for the eye of the observer is a best possible correction for a distance $A_S$≤1 m of an object from the corneal vertex of the eye for the viewing direction, wherein the additional dioptric power component has an additional negative astigmatic power for the eye of the observer and wherein the additional negative astigmatic power is a cylindrical refractive power BK with $-1.0$ DC≤BK≤$-0.125$ DC, preferably $-0.7$ DC≤BK≤$-0.3$ DC, particularly preferably BK≈$-0.5$ DC and with an axis location φ, specified in the TABO scheme, with $-20°≤φ≤20°$, preferably $-10°≤φ≤10°$, particularly preferably φ≈0°. Here, the inventors have identified that this specific astigmatism in the case of a progressive addition lens has a very positive effect on the distribution of the astigmatisms in a near region because this is connected to a broadening of the near visual field in the near region.

Then, the ascertained first parameterization may also be corrected by a dioptric power component with a spherical refractive power SBK for the viewing direction which has been reduced by the value ΔSBK, with $-1.0$ D≤ΔSBK≤$-0.1$ D, in relation to a power which, for a distance 25 cm≤$A_S$≤40 cm, preferably $A_S \approx 33$ cm of an object from the corneal vertex of the eye, corrects the eye of the observer to the best possible extent.

The best possible correction for the eye of the observer may then, additionally, also be a best possible correction for a distance $A_S \geq 4$ m of an object from the corneal vertex of the eye for a further viewing direction. Then, the first parameterization of the optical visual aid is also ascertained therefrom and the first parameterization ascertained thus is corrected by an additional dioptric power component. Then, the corrected first parameterization is set as the sought parameterization. Here, the additional dioptric power component for the eye of the observer, by which the first parameterization is corrected, is a negative astigmatic power for the further viewing direction with the cylindrical refractive power BK with $-1.0$ DC$\leq$BK$\leq -0.125$ DC, preferably $-0.7$ DC$\leq$BK$\leq -0.3$ DC, particularly preferably BK$\approx -0.5$ DC, and with an axis location $\varphi$, specified in the TABO scheme, with $70° \leq \varphi \leq 110°$, preferably $80° \leq \varphi \leq 100°$, particularly preferably $\varphi \approx 90°$ or with $-20° \leq \varphi \leq 20°$, preferably $-10° \leq \varphi \leq 10°$, particularly preferably $\varphi \approx 0°$.

The best possible correction for the eye of the observer may also be a best possible correction for a distance $A_S \geq 4$ m of an object from the corneal vertex of the eye for the viewing direction. Then, the additional dioptric power component may have an additional negative astigmatic power for the eye of the observer, wherein the additional negative astigmatic power for the viewing direction is a cylindrical refractive power BK with $-1.0$ DC$\leq$BK$\leq -0.125$ DC, preferably $-0.7$ DC$\leq$BK$\leq -0.3$ DC, particularly preferably BK$\approx -0.5$ DC, and with an axis location $\varphi$, specified in the TABO scheme, with $70° \leq \varphi \leq 110°$, preferably $80° \leq \varphi \leq 100°$, particularly preferably $\varphi \approx 90°$ or with $-20° \leq \varphi \leq 20°$, preferably $-10° \leq \varphi \leq 10°$, particularly preferably $\varphi \approx 0°$.

The disclosure also extends to a computer program including program code for carrying out the steps of the method specified above, and to a data medium comprising such a computer program. Then, a computer with a processor and a memory is present. The computer program with program code is stored in the memory. In the computer, the processor carries out the method according to the disclosure on the basis of the program code of the computer program stored in the memory.

Moreover, the disclosure also extends to a computer program product including program code stored on a computer-readable data memory to carry out the steps of the aforementioned methods. Moreover, the disclosure extends to a computer program product which can carry out the steps of the aforementioned method via the Internet or comparable networks, independently of the location of capturing the best possible correction of the eye of the observer.

A system according to the disclosure for ascertaining a sought parameterization of an optical visual aid for an eye of an observer may comprise a measuring device for determining a best possible correction of the eye accommodated onto a predetermined distance ($A_S$). Then, such a system according to the disclosure contains a computer unit, to which the best possible correction of the eye accommodated onto a predetermined distance ($A_S$), determined by the measuring device, is suppliable. The computer unit contains a computer program for ascertaining the sought parameterization ($P_E$) from the supplied best possible correction using a method specified above.

A system according to the disclosure for ascertaining a sought parameterization of an optical visual aid for an eye of an observer may also contain a device for displaying optotypes at different distances As from the corneal vertex of the eye of the observer with a device for the best possible correction of the eye of the observer at the different distances $A_S$. Such a system also contains a measuring device for determining the distance $A_S$ from optotypes shown to the observer to the corneal vertex of the eye of the observer. The system preferably has an OLED display for displaying optotypes of different dimensions for determining the eyesight of the eye of the observer. In an advantageous embodiment, the system has a display displaying the optotypes in the form of letters strung together to form words or sentences. In a particular advantageous embodiment, the system has a switching element which is actuatable by the observer and operatively coupled to a computer unit and which serves to produce an information signal, supplied to the computer unit, about the depth of field (ST) perceived by the observer.

In particular, the disclosure also relates to the use of an optical visual aid (6) comprising at least one spectacle lens (10) by an observer (28) for looking at an object (15), wherein the optical visual aid (6) has a dioptric power matched to an eye (11, 11') of the observer (28) for at least one viewing direction (A, B), the dioptric power being composed of a plurality of dioptric power components ($K_1$, $K_2$, $K_3$, $K_4$), wherein a first dioptric power component ($K_1$, $K_3$) of the plurality of dioptric power components ($K_1$, $K_2$, $K_3$, $K_4$) has a best possible corrective power for the viewing direction (A, B) for the eye (11, 11') of the observer (28) at a defined distance $A_S$ of the object (15) from the corneal vertex of the eye (11, 11'); and a further dioptric power component ($K_2$, $K_4$) of the plurality of dioptric power components ($K_1$, $K_2$, $K_3$, $K_4$) has an additional astigmatic, partly corrective power for the viewing direction (A, B) for the eye (11, 11') of the observer (28) at the defined distance $A_S$, wherein the best possible corrective power of a dioptric power component of the dioptric power of the visual aid is understood to mean the property of the dioptric power component that the contribution of the dioptric power component to the dioptric power of the visual aid overall compensates the so-called habitual refraction deficit of the observer at least to ⅕ D or to ⅛ D of the spherical power and at least to ⅕ DC or to ⅛ DC of the astigmatic power and ±5° axis location, and wherein the partly corrective power of a dioptric power component of the dioptric power of the visual aid is understood to mean the property of this dioptric power component that the contribution of the dioptric power component to the dioptric power of the visual aid overall at least partly corrects the so-called habitual refraction deficit of the observer, wherein, on account of the merely partly corrective power, the visual acuity of the observer is reduced by no more than 0.2 log MAR in relation to the visual acuity obtained by means of a dioptric power component having a best possible corrective power.

This use may include that the first dioptric power component ($K_1$) has a power which, for a distance $A_S \geq 4$ m of the object (15) from the corneal vertex of the eye (11, 11'), corrects the eye (11, 11') of the observer (28) to the best possible extent for the viewing direction (A) and the further dioptric power component ($K_2$) has an additional negative astigmatic power for the eye (11, 11') of the observer (28) for the viewing direction (A), wherein the additional negative astigmatic power is a cylindrical refractive power BK with $-1.0$ DC$\leq$BK$\leq -0.125$ DC or $-0.7$ DC$\leq$BK$\leq -0.3$ DC or BK$\approx -0.5$ DC and with an axis location $\varphi$, specified in the TABO scheme, with $70° \leq \varphi \leq 110°$ or $80° \leq \varphi \leq 100°$ or $\varphi \approx 90°$, or with an axis location $\varphi$, specified in the TABO scheme, with $-20° \leq \varphi \leq 20°$ or $-10° \leq \varphi \leq 10°$ or $\varphi \approx 0°$.

This use may also be characterized in that the first dioptric power component ($K_3$) has a power which, for a distance $A_S \leq 1$ m of the object (15) from the corneal vertex of the eye (11, 11'), corrects the eye (11, 11') of the observer (28) to the best possible extent for the viewing direction (B) and the further dioptric power component ($K_4$) has an additional negative astigmatic power for the eye (11, 11') of the observer (28) for the viewing direction (B), wherein the additional negative astigmatic power has a cylindrical refractive power BK with $-1.0$ DC$\leq$BK$\leq-0.125$ DC or $-0.7$ DC$\leq$BK$\leq-0.3$ DC or BK$\approx-0.5$ DC and an axis location $\varphi$, specified in the TABO scheme, with $-20° \leq \varphi \leq 20°$ or $-10° \leq \varphi \leq 10°$ or $\varphi \approx 0°$.

In a development, this use may be characterized in that the first dioptric power component ($K_3$) has a spherical refractive power SBK for the viewing direction (B) which has been reduced by the value $-1.0$ D$\leq \Delta$SBK$\leq-0.1$ D in relation to a power which, for a distance 25 cm$\leq$AS$\leq$40 cm or AS$\approx$33 cm of an object (15) from the corneal vertex of the eye (11, 11'), corrects the eye (11, 11') of the observer (28) to the best possible extent.

The use may also include that the dioptric power matched to the eye (11, 11') of the observer (28) is composed of at least two first and two further dioptric power components ($K_1, K_2, K_3, K_4$), wherein one of the two first dioptric power components ($K_1$) has a power which, for a distance $A_S \leq 1$ m of the object (15) from the corneal vertex of the eye (11, 11'), corrects the eye (11, 11') of the observer (28) to the best possible extent for the viewing direction (B) and the other one of the two first dioptric power components ($K_3$) has a power which, for a distance $A_S \geq 4$ m of the object (15) from the corneal vertex of the eye (11, 11'), corrects the eye (11, 11') of the observer (28) to the best possible extent for a further viewing direction (A), and wherein one of the two second dioptric power components ($K_2$) has an additional negative astigmatic, partly corrective power for the eye (11, 11') of the observer (28) with a cylindrical refractive power BK with $-1.0$ DC$\leq$BK$\leq-0.125$ DC or $-0.7$ DC$\leq$BK$\leq-0.3$ DC or BK$\approx-0.5$ DC and an axis location $\varphi$, specified in the TABO scheme, with $-20° \leq \varphi \leq 20°$ or $-10° \leq \varphi \leq 10°$ or $\varphi \approx 0°$ for the viewing direction (B), and wherein the other one of the two second dioptric power components ($K_4$) has an additional negative astigmatic power for the eye (11, 11') of the observer (28) with a cylindrical refractive power BK with $-1.0$ DC$\leq$BK$\leq-0.125$ DC or $-0.7$ DC$\leq$BK$\leq-0.3$ DC or BK$\approx-0.5$ DC and an axis location $\varphi$, specified in the TABO scheme, with $70° \leq \varphi \leq 110°$ or $80° \leq \varphi \leq 100°$ or $\varphi \approx 90°$ for the further viewing direction (A).

The use may further include that the one of the two first dioptric power components ($K_1$) with the power which, for the distance $A_S \leq 1$ m, corrects the eye (11, 11') to the best possible extent has a spherical refractive power SBK for the viewing direction (B) which has been reduced by the value $-1.0$ D$\leq \Delta$SBK$\leq-0.1$ D in relation to a power which, for a distance 25 cm$\leq A_S \leq 40$ cm, preferably $A_S \approx 33$ cm of the object (15) from the corneal vertex of the eye (11, 11'), corrects the eye (11, 11') of the observer (28) to the best possible extent.

Moreover, the disclosure relates, in particular, to a method for ascertaining a sought parameterization ($P_E$) of an optical visual aid (6) for an eye (11, 11') of an observer (28), wherein a first parameterization ($P_A$) of the dioptric power of the optical visual aid (6) in accordance with a first power component ($K_1, K_2$), which has a best possible corrective power, is determined from a best possible correction of the eye (11, 11') of the observer (28) for at least one defined distance $A_S$ of an object (15) from the corneal vertex of the eye (11, 11') for one viewing direction (A, B), the ascertained first parameterization ($P_A$) is corrected by an additional further dioptric power component ($K_2, K_4$), which has an additional astigmatic, partly corrective power for the viewing direction (A, B) at the defined distance (A3), the corrected first parameterization ($P_A$) is set as the sought parameterization ($P_E$), wherein the best possible corrective power of a dioptric power component of the dioptric power of the visual aid is understood to mean the property of the dioptric power component that the contribution of the dioptric power component to the dioptric power of the visual aid overall compensates the so-called habitual refraction deficit of the observer at least to $\frac{1}{5}$ D or to $\frac{1}{8}$ D of the spherical power and at least to $\frac{1}{5}$ DC or to $\frac{1}{8}$ DC of the astigmatic power and $\pm 5°$ axis location, and wherein the partly corrective power of a dioptric power component of the dioptric power of the visual aid is understood to mean the property of this dioptric power component that the contribution of the dioptric power component to the dioptric power of the visual aid overall at least partly corrects the so-called habitual refraction deficit of the observer, wherein, on account of the merely partly corrective power, the visual acuity of the observer is reduced by no more than 0.2 log MAR in relation to the visual acuity obtained by means of a dioptric power component having a best possible corrective power.

This method may include that the best possible correction for the eye (11, 11') of the observer (28) for the viewing direction (B) is a best possible correction for a distance $A_S \leq 1$ m or 25 cm$\leq A_S \leq 40$ cm or $A_S \approx 25$ cm or $A_S \approx 33$ cm or $A_S \approx 40$ cm of an object (15) from the corneal vertex (11, 11') of the eye and the additional dioptric power component ($K_4$) has an additional negative astigmatic power for the eye (11, 11') of the observer (28), wherein the additional negative astigmatic power is a cylindrical refractive power BK with $-1.0$ DC$\leq$BK$\leq-0.125$ DC, preferably $-0.7$ DC$\leq$BK$\leq-0.3$ DC, particularly preferably BK$\approx-0.5$ DC and with an axis location $\varphi$, specified in the TABO scheme, with $70° \leq \varphi \leq 110°$ or $80° \leq \varphi \leq 100°$, particularly preferably $\varphi \approx 90°$, or an axis location $\varphi$ with $-20° \leq \varphi \leq 20°$ or $-10° \leq \varphi \leq 10°$ or $\varphi \approx 0°$.

The method may further include that the ascertained first parameterization ($P_A$) is corrected by a dioptric power component with a spherical refractive power SBK which has been reduced by the value $\Delta$SBK, with $-1.0$ D$\leq \Delta$SBK$\leq-0.1$ D, in relation to a power which, for a distance 25 cm$\leq A_S \leq 40$ cm or $A_S \approx 33$ cm of an object (15) from the corneal vertex of the eye (11, 11'), corrects the eye (11, 11') to the best possible extent.

The method may moreover include that the best possible correction for the eye (11, 11') of the observer (18) additionally is a best possible correction for a distance $A_S \geq 4$ m of an object (15) from the corneal vertex (11, 11') of the eye for a further viewing direction (B) and the first parameterization ($P_A$) of the optical visual aid (10) is also ascertained therefrom, and the first parameterization ($P_A$) ascertained thus is also corrected by an additional dioptric power component ($K_3$) and the corrected first parameterization ($P_A$) is set as the sought parameterization ($P_E$), wherein the additional dioptric power component ($K_3$) for the eye (11, 11') of the observer (28) is a negative astigmatic power with the cylindrical refractive power BK with $-1.0$ DC$\leq$BK$\leq-0.125$ DC or $-0.7$ DC$\leq$BK$\leq-0.3$ DC or BK$\approx-0.5$ DC and with an axis location $\varphi$, specified in the TABO scheme, with $70° \leq \varphi \leq 110°$ or $80° \leq \varphi \leq 100°$ or $\varphi \approx 90°$, or with $-20° \leq \varphi \leq 20°$ or $-10° \leq \varphi \leq 10°$ or $\varphi \approx 0°$.

Here, the method may also be include that the best possible correction for the eye (11, 11') of the observer (28) for the viewing direction (A) is a best possible correction for a distance $A_S \geq 4$ m of an object (15) from the corneal vertex (11, 11') of the eye and the additional dioptric power component ($K_3$) has an additional negative astigmatic power for the eye (11, 11') of the observer (28), wherein the additional negative astigmatic power is a cylindrical refractive power BK with $-1.0 \text{ DC} \leq \text{BK} \leq -0.125 \text{ DC}$, preferably $-0.7 \text{ DC} \leq \text{BK} \leq -0.3 \text{ DC}$, particularly preferably $\text{BK} \approx -0.5 \text{ DC}$ and with an axis location $\varphi$, specified in the TABO scheme, with $70° \leq \varphi \leq 110°$, preferably $80° \leq \varphi \leq 100°$, particularly preferably $\varphi \approx 90°$.

The disclosure also relates to a computer program including program code for carrying out all steps of a method specified above.

Moreover, the disclosure relates to a system (92) for ascertaining a sought parameterization ($P_E$) of an optical visual aid (10) for an eye (11, 11') of an observer (28), comprising a measuring device (94) for determining a best possible correction of the eye (11) accommodated onto a predetermined distance ($A_S$); and comprising a computer unit (98), to which the best possible correction of the eye (11) accommodated onto a predetermined distance ($A_S$), determined by the measuring device (94), is suppliable; which includes that the computer unit contains a computer program for ascertaining the sought parameterization ($P_E$) from the supplied best possible correction using a computer program specified above.

The disclosure also relates to a system for ascertaining a sought parameterization of an optical visual aid (10) for an eye (11, 11') of an observer (28), comprising a device (30) for the best possible correction of the eye (11, 11') of the observer (28) at the different distances $A_S$; and comprising a measuring device for determining the distance $A_S$ from optotypes shown to the observer (28) to the corneal vertex of the eye (11, 11') of the observer (28).

Here, the system may be include a display (38) for displaying optotypes (36) of different dimensions for determining the eyesight of the eye (11, 11') of the observer (28) and/or a display (38) displaying optotypes in the form of letters strung together to form words or sentences and/or a switching element (28) which is actuatable by the observer and operatively coupled to a computer unit (42) and which serves to produce an information signal, supplied to the computer unit (42), about the depth of field (ST) perceived by the observer (28).

BRIEF DESCRIPTION OF THE DRAWINGS

Below, advantageous exemplary embodiments of the disclosure, which are schematically depicted in the drawings, are described, wherein.

DESCRIPTION OF EXEMPLARY EMBODIMENTS

FIGS. 11A to 11E show the influence of an additional astigmatic power on the profile of the surface astigmatisms in the case of a progressive addition lens.

Figure 1:
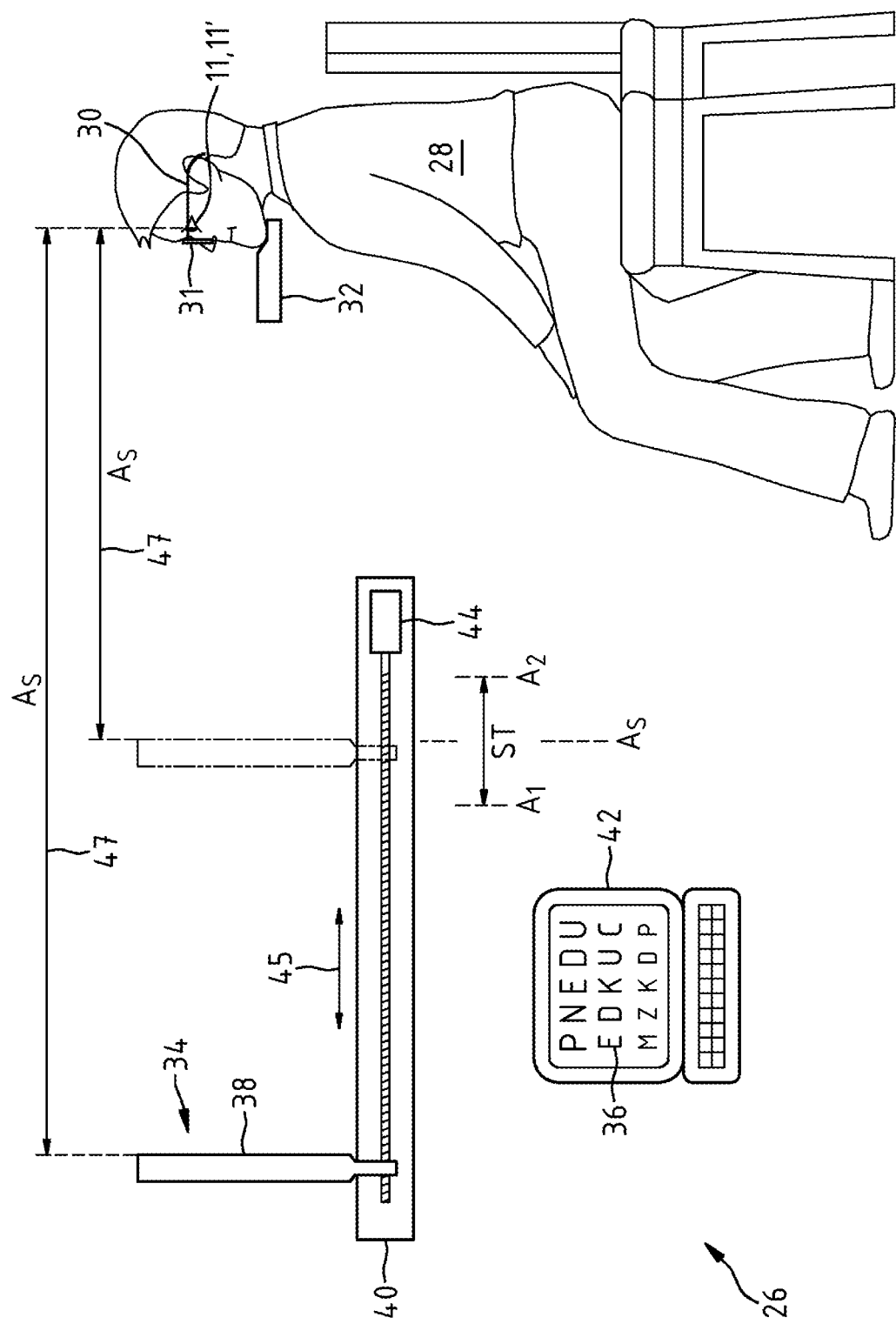
FIG. 1 shows a first system for ascertaining a parameterization of an optical visual aid with an additional astigmatic power in respect of the compensation of refraction at a defined distance.

FIG. 1 shows a first system 26 for ascertaining a parameterization of an optical visual aid with an additional astigmatic power for the eyes 11, 11' of an observer 28 in relation to the compensation of refraction at a defined distance $A_S$ of an object from the corneal vertex of the eyes 11, 11' of the observer.

The system 26 comprises testing spectacles 30 with interchangeable testing lenses 31. By inserting suitable testing lenses 31 into the testing spectacles 30, it is possible to set a spherical refractive power and a cylindrical refractive power and a prismatic power for the left eye 11 and right eye 11' of the observer 28 to provide the best possible correction for the corresponding eye 11, 11'. In the system 26, there is a chin support 32, which is used to keep the head of the observer 28 stationary. The system 26 further comprises a visualization apparatus 34 for displaying different optotypes 36 on an OLED display 38 for the left eye 11 and right eye 11' of the observer 28. The system 26 contains a computer unit 42 connected to the OLED display 38, for adjusting the type and size of optotypes on the OLED display 38.

The OLED display 38 in the system 26 is held on a rail 40. There, it is guided in a linearly movable manner in relation to the chin support 32 and, in accordance with the double-headed arrow 45, may be positioned at a plurality of different distances 47 from the eyes 11, 11' of the observer 28 with a stepper motor 44 controlled by the computer unit 42. With this, different distances $A_S$ of the optotypes from the corneal vertex of the eyes 11, 11' of the observer may be displayed for the optotypes displayed on the OLED display 38.

Hence, the system 26 facilitates a determination of the depth of field ST of the visual impression of an observer 28 for different distances $A_S \approx 25$ cm, $A_S \approx 33$ cm, $A_S \approx 40$ cm, $A_S \approx 55$ cm, $A_S \approx 66.7$ cm, $A_S \approx 100$ cm, $A_S \approx 4$ m, by virtue of appropriate optotypes being shown to the observer on the OLED display 38 at different distances $A_S$ with different parameterizations of the testing spectacles 30. Here, the depth of field ST is the difference ST=A1−A2 between a first distance A1 and a second distance A2<A1 of the OLED display 38 from the eyes 11, 11' of the observer 28, at which the observer is just still able to identify optotypes displayed on the OLED display 38, the size of which has been increased by 0.1 log MAR in relation to the maximum visual acuity of the observer, with the visual acuity then being reduced by 0.1 log MAR. It should be noted that the maximum visual acuity for a healthy human usually has at least the value of 0.0 log MAR.

Figure 2:
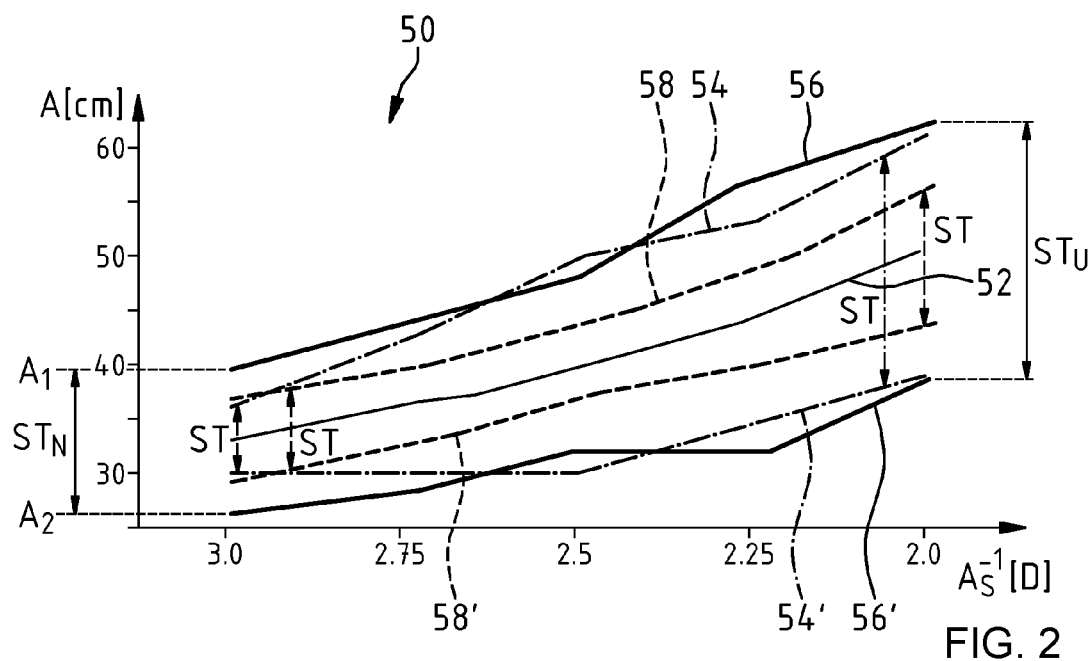
FIG. 2 shows a graph with experimental values of the depth of field perceived at different distances by an observer as a result of a spectacle lens with an additional astigmatic power in respect of the compensation of refraction.

FIG. 2 shows a graph 50 with experimental values for the depth of field ST perceived by an observer 28 through the testing spectacles 30 in the case of different spherical powers of the lenses arranged therein. For a distance of the OLED display 38 from the eyes 11, 11' of the observer 28 corresponding to the curve 52, the lenses of the testing spectacles 30 cause a complete compensation of refraction on account of the parameterization thereof with the spherical power specified along the abscissa. Here, the curves 54, 54' correspond to the depth of field ST perceived by the observer 28 without the additional astigmatism of the lenses. The curves 56, 56' show the depth of field perceived by the observer 28 in the case of a dioptric power of the lenses of the testing spectacles 30, on which the curve 52 is based, with an additional astigmatism having the cylindrical refractive power of −0.5 DC and the axis location of $\varphi=0°$ in relation to the TABO scheme. The curves 58, 58' correspond to the depth of field perceived by the observer 28 in the case of a dioptric power of the lenses of the testing spectacles 30, on which the curve 52 is based, with an additional astigmatism of the cylindrical refractive power of −0.5 DC and the axis location of $\varphi=90°$ in relation to the TABO scheme.

As the graph 50 shows, the depth of field ST perceived by the observer 28 may be increased in the distance range lying in the vicinity of the eyes of the observer 28 by way of the additional astigmatism of the lenses of the testing spectacles 30 if the additional astigmatism has the cylindrical refractive power of −0.5 DC and the axis location of $\varphi=90°$ in relation to the TABO scheme. In the case of large distances A from the eyes of the observer 28, i.e. A≥1 m, the depth of field ST perceived by the observer 28 is increased with an additional astigmatism of the testing spectacles 30 with the cylindrical refractive power of −0.5 DC and the axis location of $\varphi=90°$ in relation to the TABO scheme.

Figure 3:
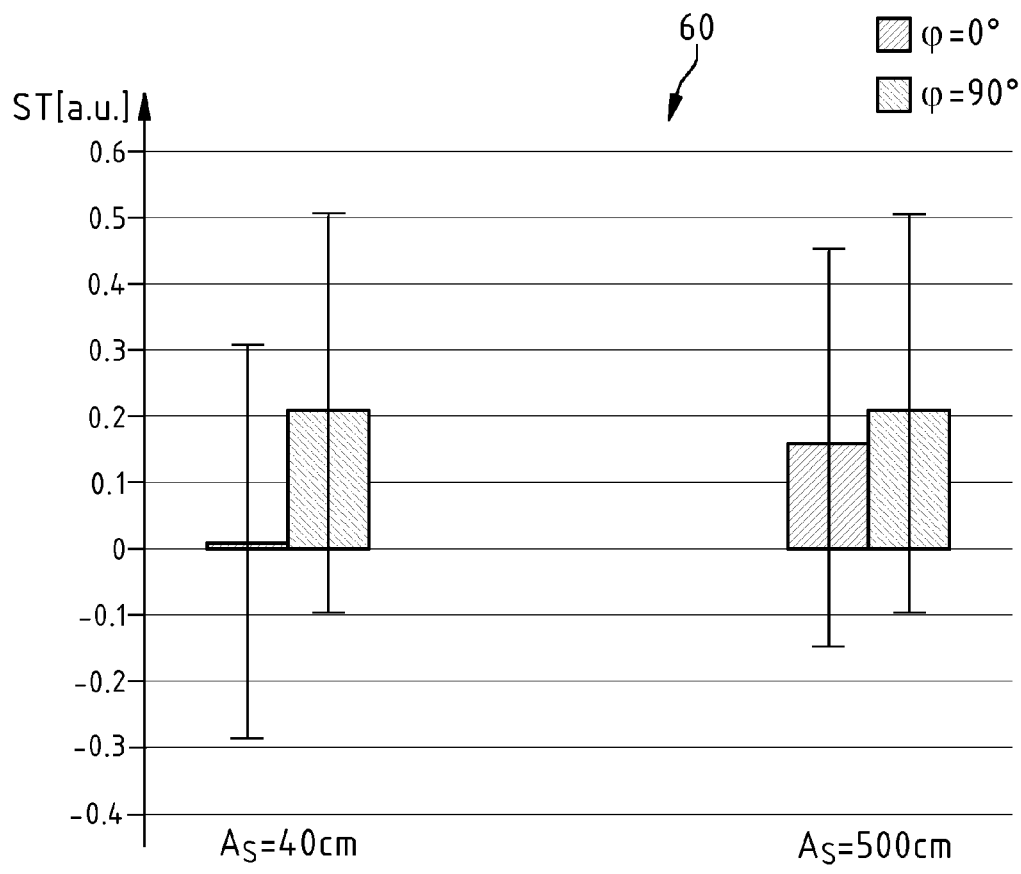
FIG. 3 shows a graph with experimental values of the depth of field perceived at different distances by various observers as a result of a spectacle lens with an additional astigmatic power in respect of the compensation of refraction.

FIG. 3 shows a graph 60 with experimental values of the depth of field ST perceived by different observers 28 through testing spectacles 30 at the distances of $A_S=40$ cm and $A_S=500$ cm. Here, in addition to a parameterization required for the compensation of refraction of the observers 28, lenses were inserted into the testing spectacles 30 which have an astigmatic power with the cylindrical refractive power of −0.5 DC and with the axis location of $\varphi=0°$ and $\varphi=90°$ in relation to the TABO scheme. As emerges from the graph 60, the increase in the depth of field ST connected with the additional astigmatism differs for different observers. However, what emerges from the graph 60 is that, on average, the perceivable depth of field ST of an observer is significantly increased with the additional astigmatism of the cylindrical refractive power of −0.5 DC and the axis location of $\varphi=90°$ in the vicinity, i.e., small distances $A_S$, and of the axis location of $\varphi=90°$ for the distance, i.e., large distances $A_S$.

Using the system 26, it is possible to ascertain a parameterization, which is expedient for an observer 28, of spectacle lenses 10 matched to the eyes 11, 11' of the observer 28, for the left and/or right eye 11, 11' for increasing the depth of field perceived by the observer for a certain viewing direction, for example as follows:

Initially, the head of the observer 28 is positioned in the chin support 32. Then, the OLED display 38 is moved to a defined target distance at which the OLED display 38 has a first distance of $A_{S1} \approx 33$ cm from the corneal vertex of the eyes 11, 11', set by an observer 28 at the computer unit 42, the distance lying in the near distance region. Then, in a first step, the correction with which a best possible correction is obtained for this distance is inserted into the testing spectacles for the observer 28. In a second step, the depth of field perceived by the observer 28 for the distance $A_S \approx 33$ cm is determined by virtue of the OLED display 38 being moved toward the observer 28 until the latter is no longer able to identify optotypes displayed on the OLED display, the size of which is increased in relation to the maximum visual acuity of the observer by 0.1 log MAR, with the visual acuity then being reduced by 0.1 log MAR. The displacement travel of the OLED display 38 connected therewith is then stored in the computer unit 42. Subsequently, the second step is repeated for distances of $A_S \approx 36$ cm, $A_S \approx 40$ cm, $A_S \approx 44$ cm and $A_S = 50$ cm. The values for the depth of field ascertained in the process are also stored in the computer unit 42. The best possible correcting correction of the eyes of the observer for 33 cm with the testing spectacles 30 is, in the process, weakened as follows in each case: by 0.25 D at the distance $A_S \approx 36$ cm, by 0.5 D at the distance $A_S \approx 40$ cm, by 0.75 D at the distance $A_S \approx 44$ cm, and by 1 D at the distance $A_S \approx 50$ cm.

Then, in a fourth step, an astigmatism of −0.5 DC at 0° and a spherical lens of 0.25 D are inserted into the testing spectacles for the observer 28 with the testing spectacles 30 in addition to the correction ascertained in the first step such that the spherical equivalent to the best possible correcting correction ascertained in the first step remains unchanged.

Thereupon, the second step and the third step are repeated in a fifth step and the data of the depth of field are then stored in the computer unit 42. Following this, in a sixth step, an astigmatism of −0.5 DC at 90° and a spherical lens of 0.25 D are inserted into the testing spectacles 30 for the observer 28 in addition to the correction from the first step such that the spherical equivalent to the best possible correcting correction from the first step remains unchanged. Thereafter, the second step and the third step are repeated in a seventh step and the data of the depth of field are stored in the computer unit 42 again.

In an eighth step, the data thus ascertained are depicted in a graph corresponding to the graph 50 from FIG. 2. Then, an addition reduction of the correction in the testing spectacles 30 is set from this graph 50 in a ninth step as follows:

The addition of the correction is reduced by that value at which the depth of field ST of the eye 11, 11' for the observer 28 still facilitates clear imaging of the optotypes at a distance of $A_S \approx 33$ cm on the abscissa of the graph.

As an alternative thereto, the system 26 may also be used to ascertain a parameterization, which is expedient for an observer 28, of spectacle lenses 10 matched to the eyes 11, 11' of the observer 28 as follows to increase the depth of field for the left eye 11 and/or right eye 11' perceived by the observer.

Initially, the head of the observer 28 is positioned in the chin support 32. Then, the OLED display 38 is moved to a defined target distance at which the OLED display 38 has a first distance of $A_S \approx 33$ cm from the corneal vertex of the eyes 11, 11', set by an observer 28 at the computer unit 42, the distance lying in the near distance region. Then, in a first step, the correction with which a best possible correction is obtained for this distance is inserted into the testing spectacles for the observer 28.

Thereafter, optotypes with a different size are displayed on the OLED display 38 in a second step and hence the eyes 11, 11' of the observer 28 are corrected for the distance $A_S$ by inserting different optical lenses 46, 48 with a spherical and/or cylindrical refractive power and/or a prismatic power into the testing spectacles 30. Here, the size of the optotypes is selected in such a way that the size thereof is not increased by more than 0.1 log MAR in relation to the maximum visual acuity of the observer 28, with the visual acuity then being reduced by 0.1 log MAR. The dioptric power required for the compensation of refraction, ascertained in the process for an eye 11, 11', is then defined in a memory of the computer unit 42 as an initial parameterization $P_A$ for a spectacle lens matched to the corresponding eye 11, 11' and stored in the memory of the computer unit 42.

Then, in a third step, the depth of field ST perceived by the observer 28 through testing spectacles 30 with lenses 46, 48 in relation to the distance $A_S$ is determined for these optical lenses 46, 48 which have a best possible corrective power for a corresponding eye 11, 11' of the observer 28 at a specific distance A.

Then, an additional optical element in the testing spectacles 30 is used in a fourth step to superpose an astigmatism with the cylindrical refractive power of −0.5 DC and 90° axis location onto the dioptric power of the ascertained initial parameterization $P_A$.

Subsequently, the distance A of the OLED display 38 from the eyes 11, 11' of the observer 28 is varied in a fifth step by displacing the OLED display 38 on the rail. By way of this, the possible displacements of the OLED display 38 from the distance $A_S \approx 5$ m, up to which the observer 28 does not perceive any change in their visual impression with one eye 11, 11' of optotypes displayed on the OLED display 38, are determined. In this way, the depth of field $ST_U$ of the visual impression for the distance, i.e., the infinite distance region, is ascertained.

The ascertained depth of field $ST_U$ is then defined as the depth of field of the visual impression of the corresponding eye 11, 11' of the observer 28 at the infinite distance region and stored in the memory of the computer unit 42.

In a sixth step, the OLED display 38 is then moved to a target distance $A_S \approx 30$ cm which differs from the first target distance $A_S$ and at which the OLED display 38 has a second distance $A_S \approx 30$ cm from the corneal vertex of the eyes 11, 11' of an observer 28 which was set by the observer 28 at the computer unit 42 and corresponds to the near distance region.

Then, a further optical element in the form of a testing lens with an astigmatic power in the testing spectacles 30 is used in a seventh step to superpose an astigmatism with the cylindrical refractive power of −0.5 DC and 0° axis location or 90° axis location onto the dioptric power of the ascertained initial parameterization $P_A$.

Thereupon, the distance A of the OLED display 38 from the corneal vertex of the eyes 11, 11' of the observer 28 is varied in an eighth step by displacing the OLED display 38 on the rail to ascertain the depth of field of the visual impression for the near distance region by determining the possible displacements of the OLED display 38 from the distance $A_S \approx 30$ cm, up to which the observer 28 does not perceive any changes in their visual impression with an eye 11, 11'.

The ascertained depth of field $ST_N$ is then defined as the depth of field of the visual impression of the corresponding eye 11, 11' of the observer 28 at the near distance region and stored in the memory of the computer unit 42.

Then, in a ninth step, a parameterization of $P_F$ is defined as the final parameterization for a spectacle lens matched to the corresponding eye 11, 11' as follows: Firstly, the parameterization $P_F$ is corrected in relation to the initial parameterization $P_A$ by a spherical power for the infinite distance region which corresponds to an object distance reduced by the ascertained depth of field $ST_U$. Secondly, the initial parameterization $P_A$ is corrected by a spherical addition for the near distance region which corresponds to an object distance increased by the ascertained depth of field $ST_N$. Moreover, in relation to a spectacle lens with the initial parameterization $P_A$, a spectacle lens with the final parameterization $P_F$ has an additional astigmatism with the cylindrical refractive power of −0.5 DC and 0° axis location or 90° axis location for the near distance region and an additional astigmatism with the cylindrical refractive power of −0.5 DC and 90° axis location or 0° axis location for the infinite distance region.

Then, the visual impression of the observer 28 is checked for the final parameterization $P_F$ in a tenth step by virtue of optotypes corresponding thereto being displayed with the OLED display 38 for both eyes 11, 11' in different distance regions.

In the system 26, optotypes in the form of letters strung together to form words or sentences are advantageous for determining a parameterization $P_F$, expedient for an observer 28, of spectacle lenses 10 for the left eye 11 and/or right eye 11' matched to the eyes 11, 11' of the observer 28. The inventors discovered that this measure also allows the influence of the reading ability to be taken into account. Using this, a high reproducibility of a parameterization $P_F$ ascertained for an observer 28 may be achieved for the method described above.

Figure 4A:
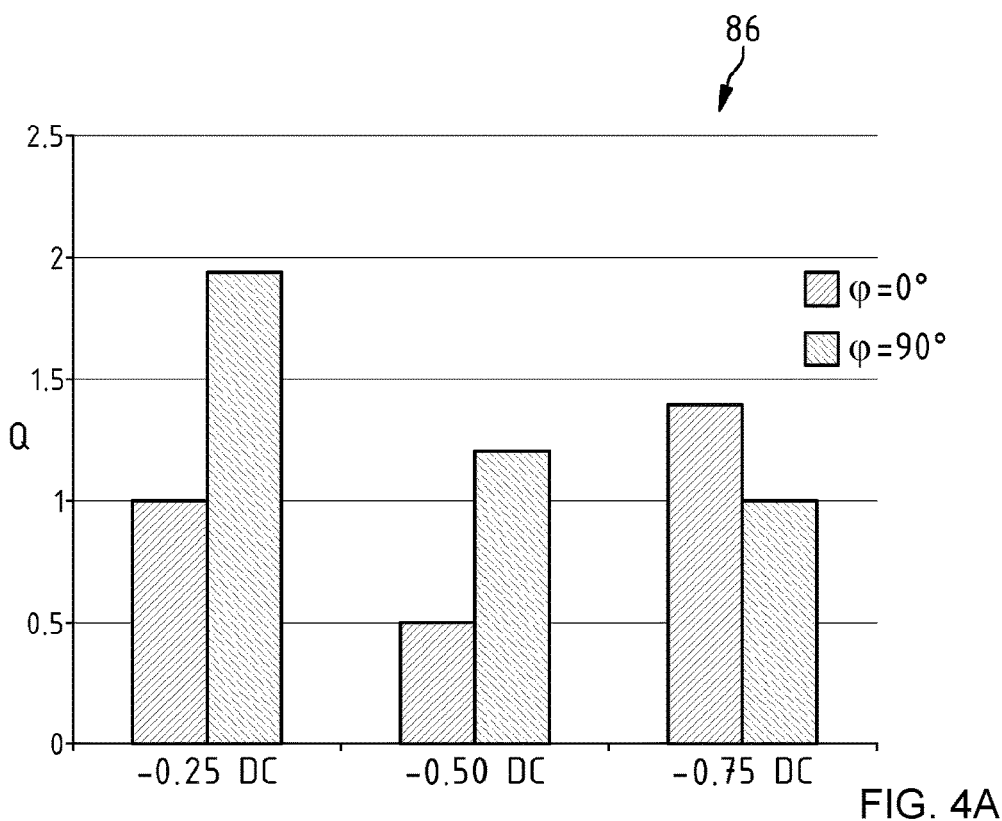
FIG. 4A shows a first graph with experimental values relating to the change in the change in the depth of field perceived by an observer when looking through a spectacle lens with an astigmatism in addition to the compensation of refraction if the visual acuity is reduced by 0.1 log MAR.

FIG. 4A shows a first graph 86 with experimental values relating to the ratio $$Q := \frac{ST_M}{ST_O}$$

of the depth of field $ST_M$ perceived by an observer 28 when observing an object at a distance of 500 cm through a spectacle lens 10 having a dioptric power composed of a first dioptric power component and a further dioptric power component to the depth of field $ST_O$ perceived by the observer 28 when observing the object through a spectacle lens 10 having a dioptric power caused by the same first dioptric power component and not having the further dioptric power component. The first dioptric power component has a best possible corrective power for the observer 28 in a defined distance region. The further dioptric power component corresponds to an astigmatism with the cylindrical refractive power BK=−0.25 DC or BK=−0.50 DC or BK=−0.75 DC and the axis location of φ=0° or φ=90° in relation to the TABO scheme. The graph 86 shows how the depth of field perceived by an observer increases if the visual acuity is reduced by 0.1 log MAR in the case of an additional astigmatism with the cylindrical refractive power BK=−0.50 DC and the axis location of φ=90° in relation to the TABO scheme.

Figure 4B:
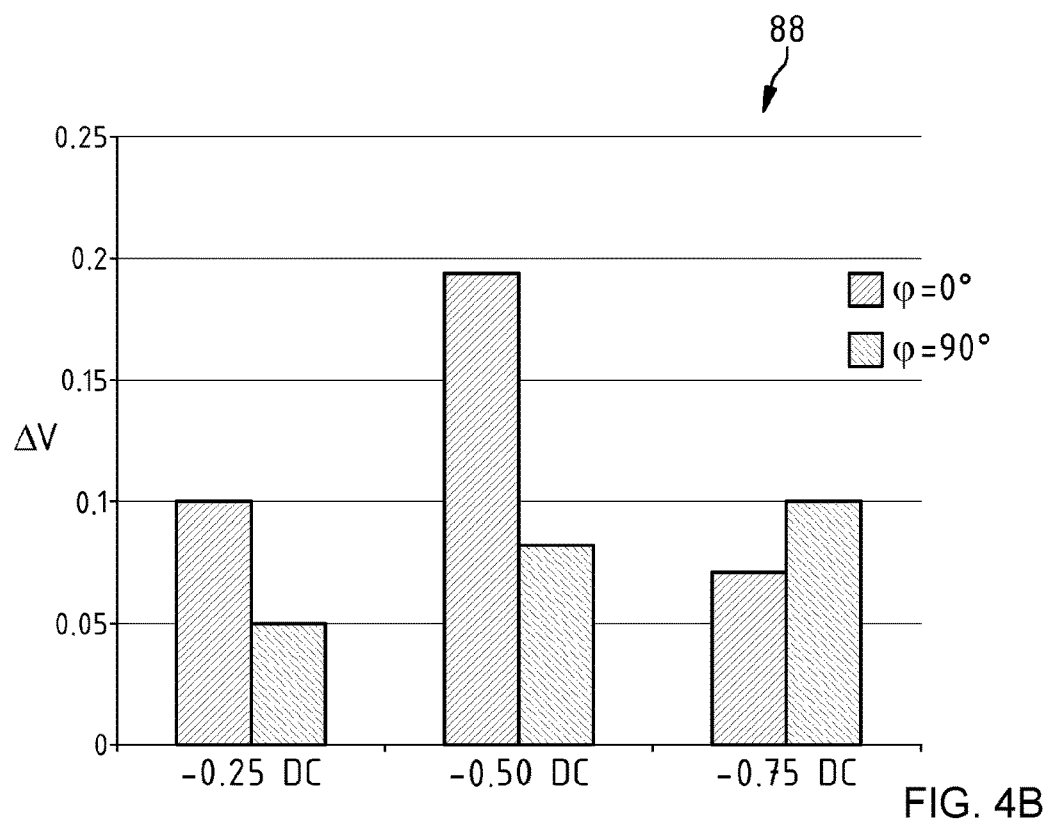
FIG. 4B shows a further graph with experimental values relating to the change in the visual acuity perceived by an observer when looking through a spectacle lens with an astigmatism in addition to the compensation of refraction if the depth of field is increased by 1 D.

In a further graph 88 with experimental values in relation to the change ΔV of the visual acuity V perceived by an observer when observing an object at a distance of 500 cm through a spectacle lens 10, which has a dioptric power composed of a first dioptric power component and a further dioptric power component, FIG. 4B shows if the depth of field is increased by 1 D. The first dioptric power component has a best possible corrective power for the observer 28 in a defined distance region. The further dioptric power component corresponds to an astigmatism with the cylindrical refractive power BK=−0.25 DC or BK=−0.50 DC or BK=−0.75 DC and the axis location of φ=0° or φ=90° in relation to the TABO scheme. The graph 88 provides evidence that the visual acuity achieved by an observer only deteriorates slightly if the depth of field is increased using an astigmatism of −0.5 DC and the axis location of φ=90° in relation to the TABO scheme.

Figure 5:
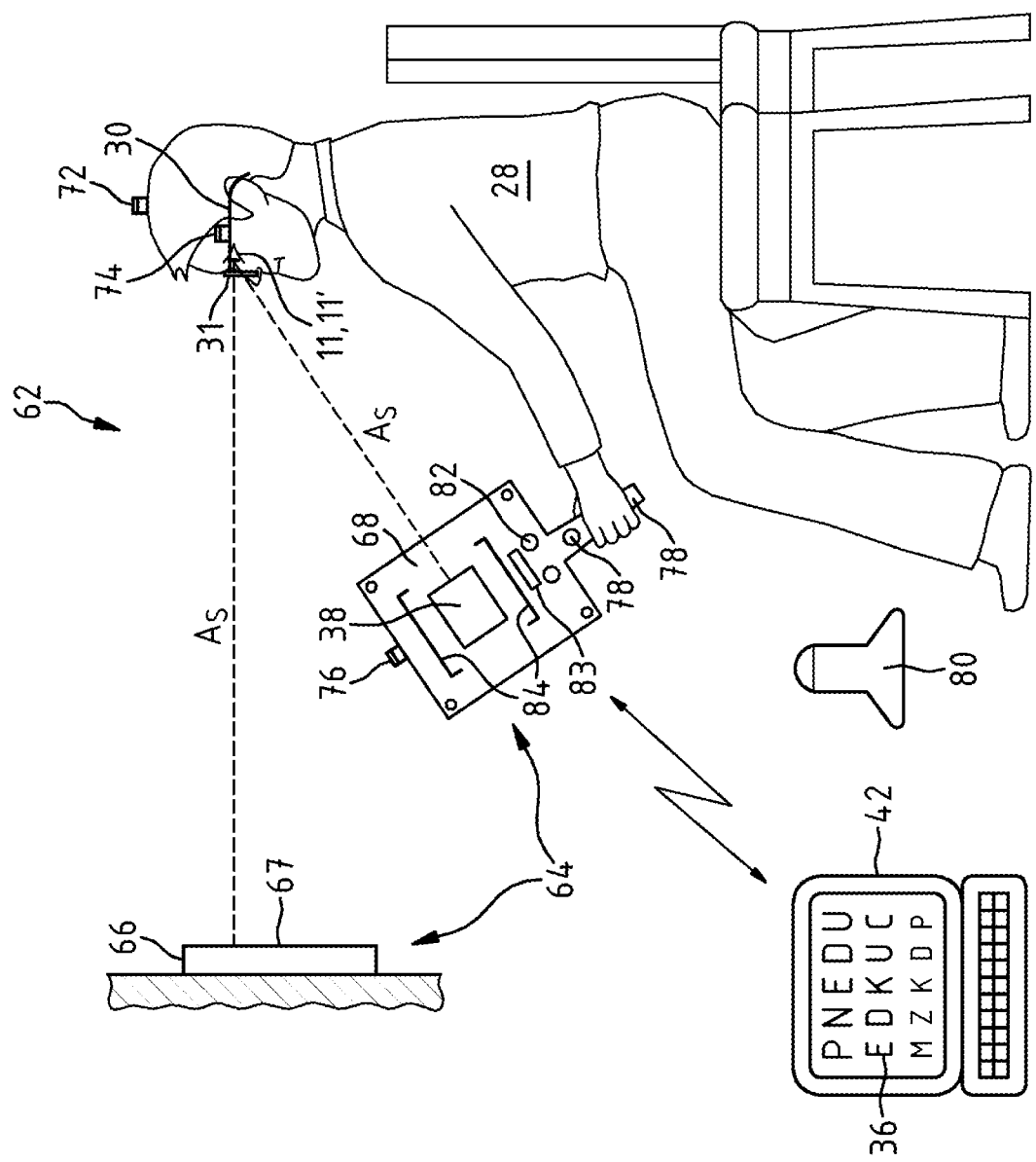
FIG. 5 shows a second system for ascertaining a parameterization of an optical visual aid with an additional astigmatic power in respect of the compensation of refraction in a defined distance region.

FIG. 5 shows a second system 62 for ascertaining a parameterization of an optical visual aid with an additional astigmatic power in respect of the compensation of refraction in a defined distance region for the eyes 11, 11' of an observer 28.

The system 62 likewise comprises testing spectacles 30. In the system 62, there is a visualization apparatus 64 comprising a first display device 66 which has a display surface 67 for displaying optotypes in the infinite distance region at a distance of $A_S \approx 5$ m from the eyes 11, 11' of the observer 28. The visualization apparatus 64 further comprises a second display device 68 with an OLED display 38 for displaying optotypes 36 in the vicinity of the eyes of the observer 28 at a distance of $A_S \approx 30$ cm. The OLED display 38 has a pixel density which, at the distance of $A_S \approx 30$ cm from the corneal vertex of the eye of the observer 28, facilitates the display of optotypes 36 with a size which allows a visual acuity to be determined with the visual acuity of −0.3 log MAR. Therefore, the OLED display 38 is, e.g., an eMAgine SVGA+Rev2 type OLED with 800×600 pixels. The display device 68 in the system 62 is configured as a reading chart panel. The display device 68 has a handle 70 that may be held in the hand by the observer 28. In the system 62, there is a position sensor 72, which is fastened to the head of the observer 28. A position sensor 74 is fastened to the testing spectacles 30. A position sensor 76 is provided at the display device 68. The system 62 contains a computer unit 42 which wirelessly communicates, for example via WLAN or Bluetooth, with the display apparatus 66 and the display device 68 and the position sensors 72, 74, and 76. A response button embodied as a pushbutton 78 is situated on the handle 70 of the display device 68. The pushbutton 78 is operatively connected to the computer unit 42.

The computer unit 42 is a measuring device for determining the distance $A_S$ from optotypes shown to the observer 28 to the corneal vertex of the eye 11, 11' of the observer 28. From the position signals transmitted from the position sensors 72, 74, 76, it calculates the relative position of the display surface 67 of the first display device 66 and the relative position of the OLED display 38 of the second display device 68 in relation to the eyes 11, 11' of the observer 28. Here, the pushbutton 78 serves to capture the information about the depth of field of his visual impression of the optotype 36 displayed with the OLED display, perceived by the observer 28 for a specific parameterization of the lenses of the testing spectacles 30. To this end, the observer 28 may communicate to the computer unit 42 by means of the pushbutton 78 the distance $A_S$ at which he is no longer able to clearly perceive optotypes displayed on the OLED display 38 in the case of a specific parameterization of the lenses of the testing spectacles 30.

In principle, the system 62 may be operated by the observer 28 or else by a third person. Thus, it facilitates, in particular the measurement of the depth of field and visual acuity of the eyes 11, 11' of the observer 28 in the near-field range in a contactless, automatic, and quick manner, without support or instructions by technicians or engineers. By way of example, the system 62 may be used by an optician. However, it is also suitable for use in clinics, research institutes, and medical practices. Using the system 62, it is possible to measure the eyes of an observer 28 in both monocular and binocular fashion. Preferably, the system 62 also contains a docking station 80 for the display device 68, which serves, for example, for charging an accumulator 83 in the display device 68.

It should be noted that the position sensors 72, 74, 76 in the system 62 may be embodied as, e.g., ultrasonic sensors. Alternatively or additionally, it is also possible to provide optical sensors for determining the relative position of the eyes of the observer in relation to the display surface 67 of the display device 66 and the display 28 of the display device 68, the optical sensors being designed to capture the corresponding distances by means of image evaluation in the computer unit 42. Using the position sensors 72, 74, 76, it is possible to record both the head position and orientation, and position and orientation of the testing spectacles 30 in a common coordinate system when the observer 28 looks onto the OLED display 38 of the display device 68 and when the observer 28 looks onto the display surface 67 of the display device 66. This facilitates the creation of individual posture profiles for observers 28 when they look through a spectacle lens.

The display device 68 may also contain a camera 82 which is arranged below the reading field and which facilitates capturing movements of the eyes of an observer 28 when reading. It should be noted that the camera 82 may also be arranged above the reading field. Here, in a particularly advantageous manner, the image sensor of the camera 82 may then also be used for determining the pupil dimension or it may act as a so-called eye tracker.

It is advantageous if the display device 68 contains an insertion frame 84 for reading text panels, by means of which the real reading behavior of an observer 28 may be tested. Here, the function of an eye tracker, as specified above, facilitates the checking of the viewing behavior. It is also advantageous to provide start-stop buttons, which serve for the quantitative detection of the reading capability of the observer 28, in the display device 68. Moreover, it is expedient if the display device 68 contains a slot for one or more color filters. This allows the observer 28 to observe the optotypes or text displayed on the OLED display 38 through a color filter.

Moreover, it should be noted that the display device 68 may optionally also comprise IR illumination LEDs which are arranged in the edge regions of the display device 68 to thereby facilitate the reflection-free illumination of the eyes of the subject.

Figure 6:
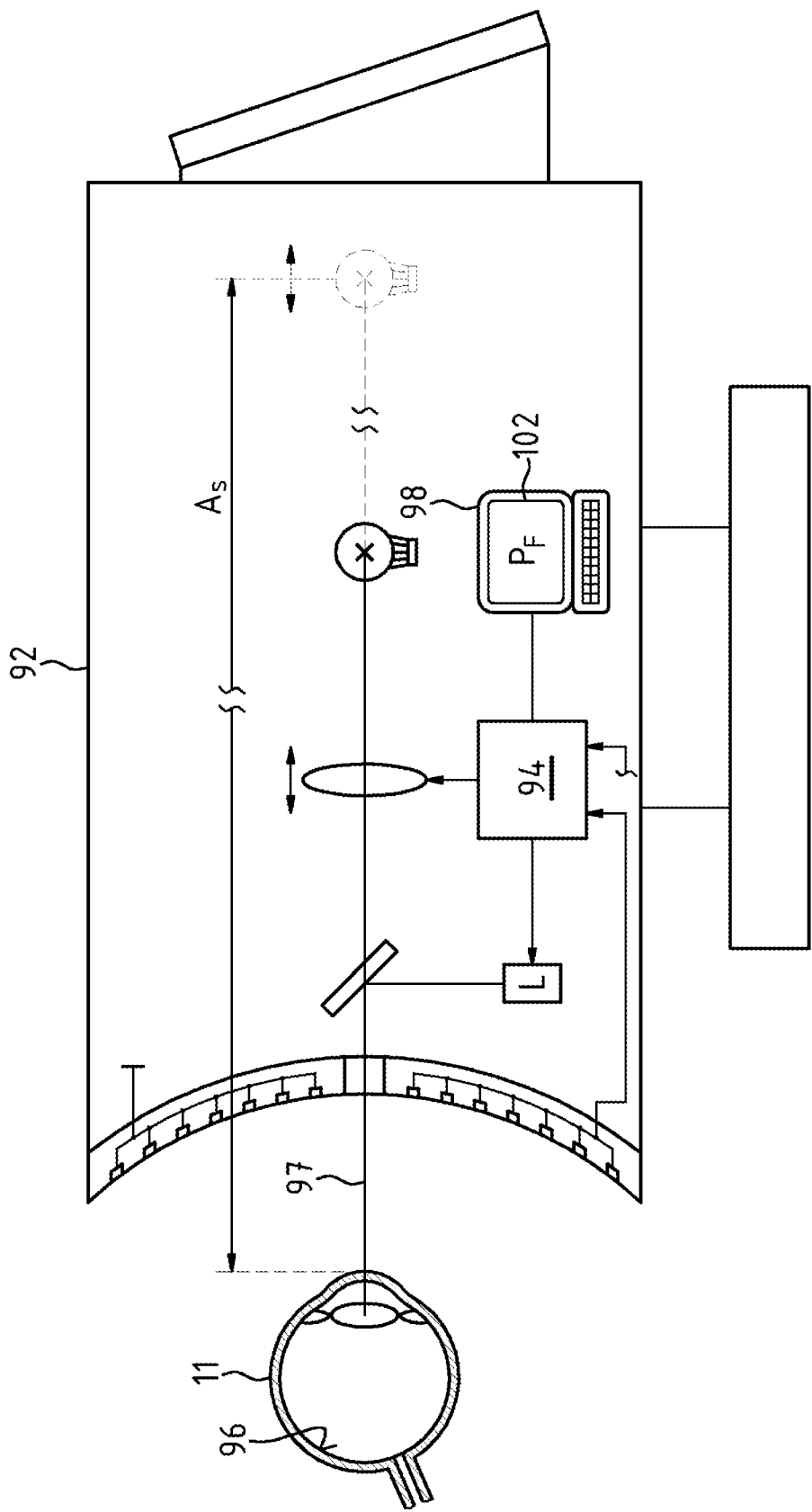
FIG. 6 shows a third system for ascertaining a parameterization of an optical visual aid with an additional astigmatic power in respect of the compensation of refraction in a defined distance region.

FIG. 6 shows a third system 92 for ascertaining a parameterization of an optical visual aid with an additional astigmatic power in respect of the compensation of refraction in a defined distance region for the eyes 11, 11' of an observer 28 for one viewing direction.

The system 92 contains a measuring device 94, as exists in, e.g., the ophthalmological measurement system i.Profiler® by Zeiss, by which, as described in detail in U.S. Pat. No. 7,744,217, a laser light beam 97 is projected onto the retina for the eye 11 of an observer 28 in a given accommodation state. Here, the wavefront of the light of the laser light beam 97 reflected by the retina 96 is captured with a wavefront measuring machine 94 and the objective habitual refraction deficit of the eye 11 is determined therefrom.

The deviation of the profile of the wavefront from a reference for an eye not afflicted by visual defects, as measured by the wavefront measuring machine 94, is then determined as the sought aberration, i.e., the deviation of the wavefront from the ideal case. By way of example, this method is described in detail in the dissertation "Änderung der optischen Aberrationen des menschlichen Auges durch Laser in situ Keratomileusis [Change in the optical aberrations of the human eye by laser in-situ keratomileusis]," by G. M. Spitzlberger, 2004, the entirety of which is referred to herewith and the entirety of the disclosure of which is incorporated into the description of this disclosure.

It should be noted that the system 92 may also contain a measuring device 94 which, as described in col. 4, lines 3 to 25, of U.S. Pat. No. 7,744,217, provides a laser beam for determining refractive errors of the eye 11 in an observer 28, the laser beam impinging on the retina of the eye through the pupil and being used to scan the retina. The light spot produced by the laser beam on the retina 96 is then captured in each case as a reflection on the macula of the eye 11.

The measuring device 94 in the system 92 is used to determine the habitual refraction deficit of the eye in two accommodation states, which correspond to the distance $A_S \approx 30$ cm and $A_S \approx 5$ m of an object from the corneal vertex of the eye 11. In principle, it should be noted that the measuring device 94 in the system 92 may be used to determine the habitual refraction deficit of the eye 11 in more than two accommodation states as well, for example accommodation states which correspond to different distances $A_S \approx 25$ cm, $A_S \approx 33$ cm, $A_S \approx 40$ cm, $A_S \approx 55$ cm, $A_S \approx 66.7$ cm, $A_S \approx 100$ cm, $A_S \approx 4$ m from the corneal vertex of the eye.

In the system 92 there is a computer unit 98, connected to the measuring device 94, with a computer program which calculates a first parameterization $P_A$ as an initial parameterization from the accommodation state corresponding to the object distance of $A_S \approx 30$ cm from the corneal vertex of the eyes 11, 11' of the observer 28. Then, the computer program corrects this first parameterization $P_A$ by an additional dioptric power component by virtue of an astigmatism with the cylindrical refractive power of −0.5 DC and 0° axis location or 90° axis location being superposed on the parameterization $P_A$. Accordingly, the computer program in the computer unit 98 calculates a further first parameterization $P_A$ as an initial parameterization from the accommodation state corresponding to the object distance of $A_S \approx 5$ m from the corneal vertex of the eyes 11, 11' of the observer 28. Then, the computer program corrects this further first parameterization $P_A$ by an additional dioptric power component by virtue of an astigmatism with the cylindrical refractive power of −0.5 DC and 90° axis location or else 0° axis location being superposed on the parameterization $P_A$.

Then, the corrected first parameterization $P_A$ and the corrected further parameterization $P_A$ are output by the computer program at an output interface 102 of the computer unit 98 as the sought final parameterization $P_F$ of the optical visual aid.

Figure 7:
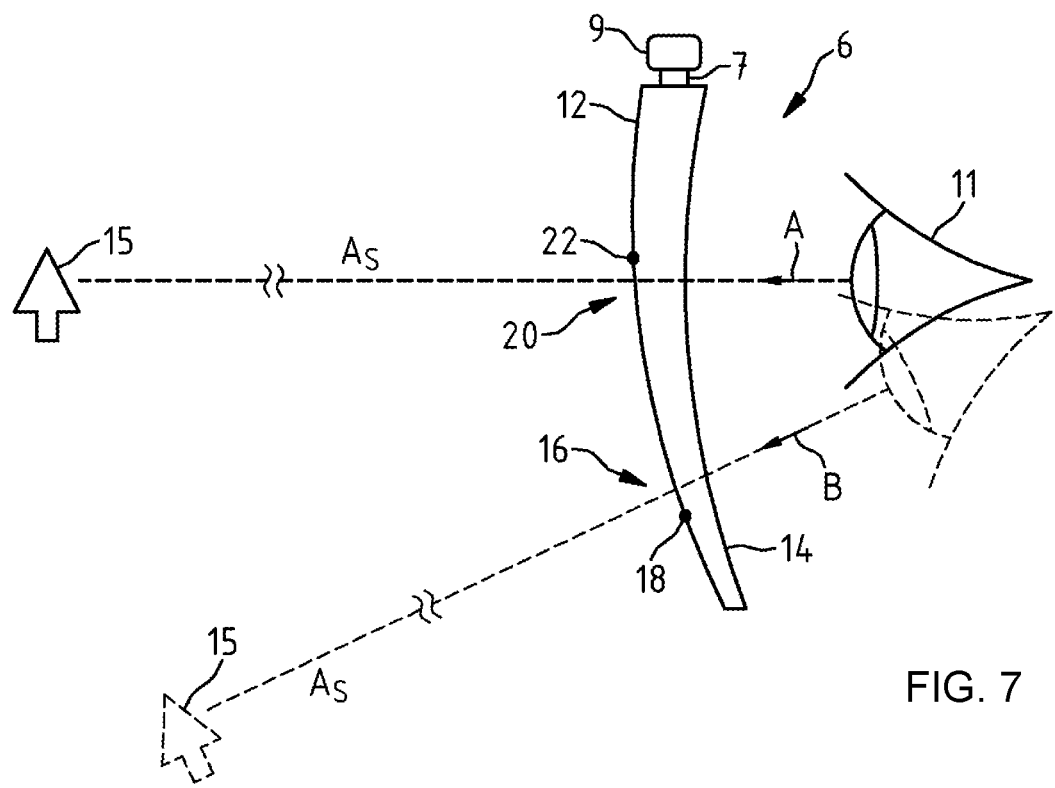
FIG. 7 shows an optical visual aid matched to an observer, comprising a spectacle lens, in a side view, with an additional astigmatic power.

FIG. 7 shows an optical visual aid 6, embodied as spectacles, for the eye 11 of an observer is a pair of spectacles. The optical visual aid 6 contains a spectacle lens 10, which is held in rims 7 on a spectacle frame 9. The spectacle lens 10 is shown in a side view in FIG. 7. Through the spectacle lens 10, an observer is able to see an object 15 at the distance $A_S$ from the corneal vertex of the eye 11 in focus by way of a viewing direction A,B passing through different regions of the spectacle lens 10. The spectacle lens 10 is a progressive addition lens. The spectacle lens 10 has a spectacle lens front surface 12 which, when used as intended, is distant from an eye 11 of an observer, and it has a spectacle lens rear surface 14 which, when used as intended, faces the eye of the observer. Here, the spectacle lens front surface 12 is designed as a progressive addition surface. The spectacle lens front surface 12 has a near region zone 16 with a near-field reference point 18 and a far region zone 20 with a far-field reference point 22. In the present case, the spectacle lens rear surface 14 is a prescription surface, i.e., sphere, cylinder and axis locations of this surface were manufactured according to the prescription of a spectacle prescription modified in accordance with embodiments above.

Figure 8:
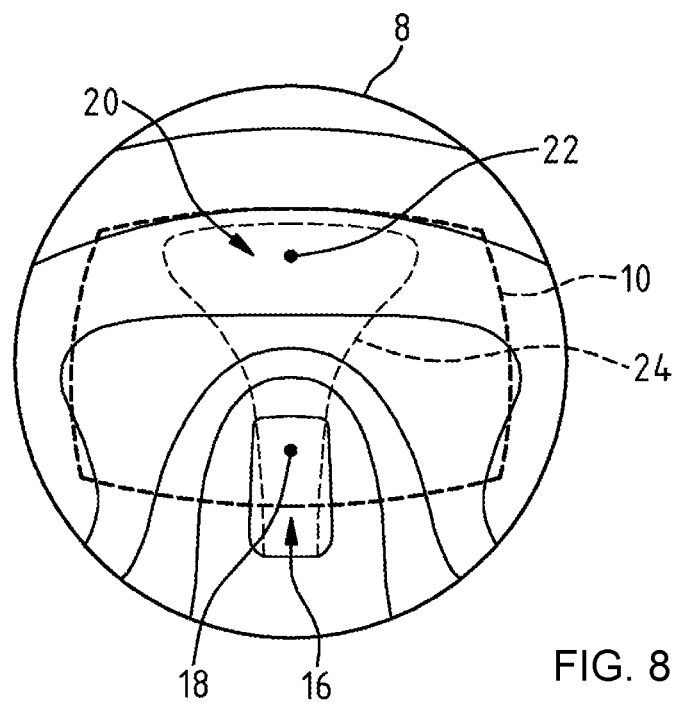
FIG. 8 shows the spectacle lens of the optical visual aid in a front view with a near-field reference point and a far-field reference point.

FIG. 8 shows the spectacle lens 10 as part of a spectacle lens blank 8 in a front view. The spectacle lens 10 is designed as a left spectacle lens 10 for the eye 11 of the observer. On the spectacle lens front surface 12, it has a near-field reference point 18 lying in a near region zone 16 and a far region zone 20 with a far-field reference point 22. A progression channel 24 extends between the near region zone 16 and the far region zone 20.

The dioptric power of the spectacle lens 10 can be decomposed at the near-field reference point 18 and at the far-field reference point 22 into a plurality of dioptric power components $K_1$, $K_2$, $K_3$, $K_4$ with different refractive powers $BKN_1$, $BKN_2$, $BKF_1$, $BKF_2$.

At the near-field reference point 18, the spectacle lens 10 has a dioptric power with the refractive power $BKN=BKN_1+BKN_2$. There, the dioptric power of the spectacle lens 10 is composed of a first dioptric power component $K_2$ with the spherical refractive power $BKN_1$ and a second dioptric power component $K_4$ with the cylindrical refractive power $BKN_2$. The first power component $K_1$ corrects the eye 11 of the observer for the vicinity in the case of a viewing direction extending through the near-field reference point 18.

Accordingly, the spectacle lens has a dioptric power with the refractive power $BKF=BKF_1+BKF_2$ at the far-field reference point 22, which is composed of a power component $K_1$ and a further power component $K_3$. The power component $K_1$ brings about the correction of the corresponding eye 11 of the observer for the distance at the far-field reference point 22.

Figure 9:
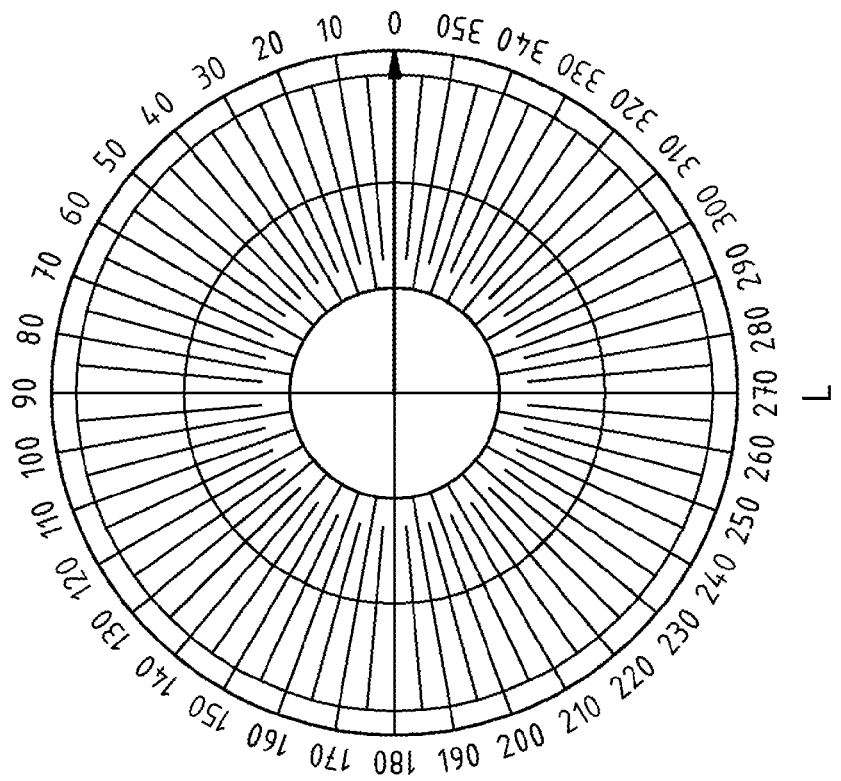
FIG. 9 shows the axis location of the additional astigmatic power in the near-field reference point according to the TABO scheme.
Figure 9:
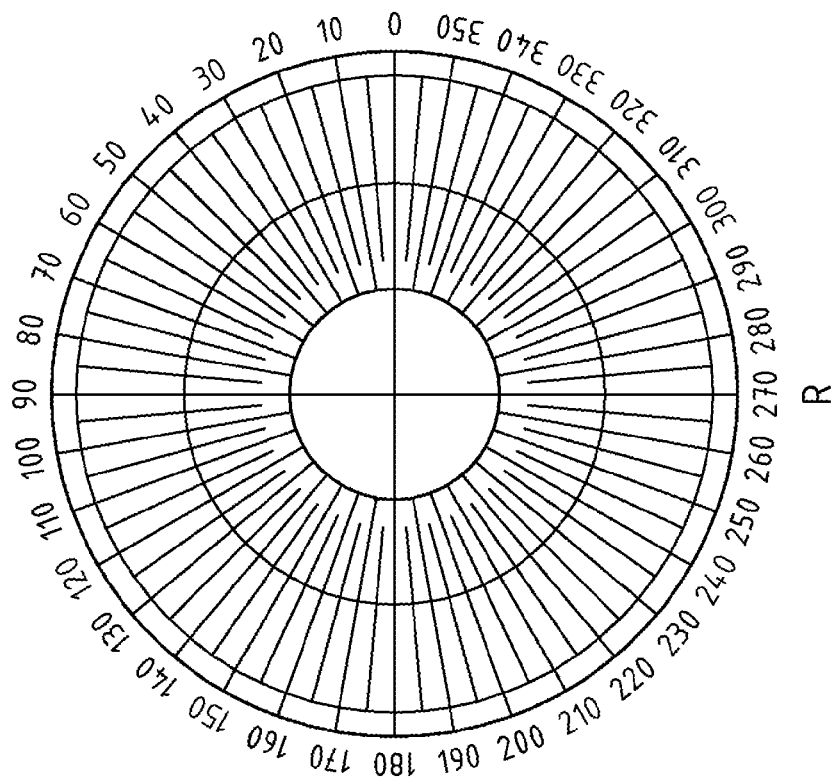
Figure 10:
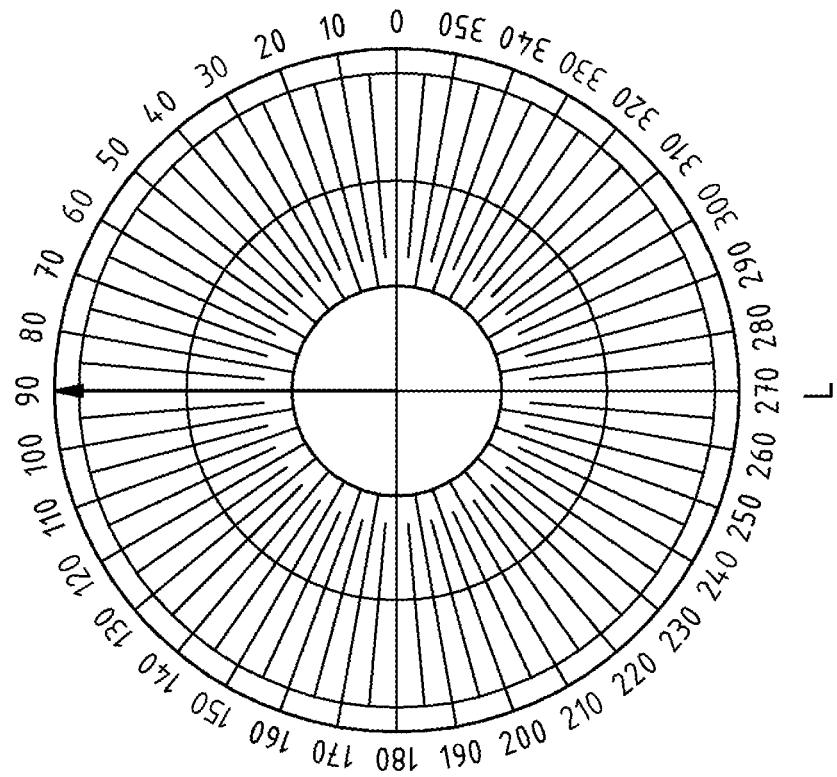
FIG. 10 shows the axis location of the additional astigmatic power in the far-field reference point according to the TABO scheme.
Figure 10:
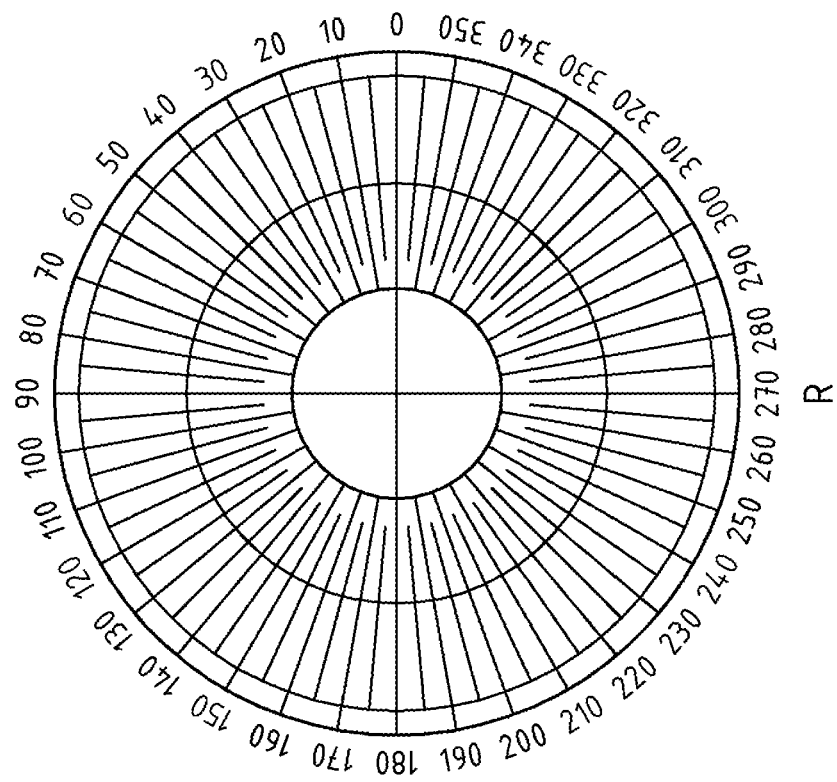

The dioptric power components $K_2$, $K_4$ each correspond to an astigmatism with the cylindrical refractive power of −0.5 DC. However, the axis location of the astigmatism of the dioptric power components $K_3$, $K_4$ differs. FIG. 9 shows the TABO scheme of the additional astigmatism of the dioptric power component $K_4$ in the near-field reference point 18. The dioptric power component $K_4$ has the cylindrical refractive power $BKN_2$ and the axis location $\varphi=0°$. FIG. 10 shows the axis location of the additional astigmatism of the dioptric power component $K_3$ of the dioptric power of the spectacle lens 10 at the far-field reference point 22. The dioptric power component $K_3$ has the cylindrical refractive power $BKF_2$ and the axis location $\varphi=90°$.

The inventors have identified that the depth of field ST for the vicinity, perceived by an observer, may be increased by virtue of an additional astigmatism with the cylindrical refractive power of −0.5 DC and the axis location of $\varphi=90°$, in relation to the TABO scheme, being superposed onto the dioptric power of a spectacle lens which corrects the eye 11 of the observer to the best possible extent for the vicinity.

Further, the inventors have identified that the depth of field for the distance, perceived by an observer, may be increased by virtue of an additional astigmatism with the cylindrical refractive power of −0.5 DC and the axis location of $\varphi=90°$ or $\varphi=0°$, in relation to the TABO scheme, being superposed onto the dioptric power of a spectacle lens which corrects the eye 11 of the observer to the best possible extent for the vicinity.

In particular, the inventors have identified that the depth of field perceived by an observer may be increased by virtue of the additional astigmatism, specified above, being superposed both onto the dioptric power of a spectacle lens which corrects the left eye of the observer to the best possible extent and onto the dioptric power of a spectacle lens which corrects the right eye of the observer to the best possible extent.

The spectacle lens rear surface 14 of the spectacle lens 10, which is a prescription surface, has a sphere matched to the observer and a cylinder with a specific axis location for producing the additional astigmatism specified above. In general, the spectacle lens rear surface 14 also comprises a further cylinder with a specific axis location to thereby compensate, e.g., an astigmatism of the eye.

FIGS. 11A to 11E explain the influence of an additional astigmatic power on the extent of the near and far region zone 16, 20 and on the progression channel 24 in the case of a progressive addition lens 10.

Figure 11C:
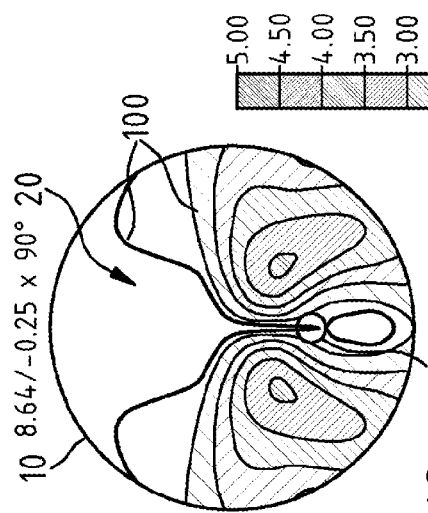
FIG. 11C shows yet another exemplary embodiment of a progressive addition lens.
Figure 11B:
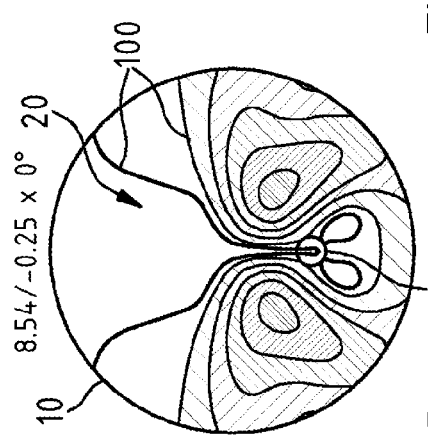
FIG. 11B shows another exemplary embodiment of a progressive addition lens.
Figure 11A:
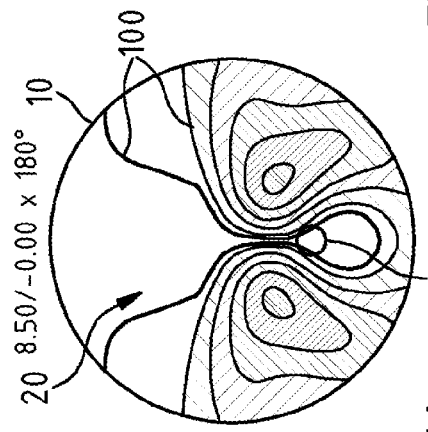
FIG. 11A shows an exemplary embodiment of a progressive addition lens.

FIG. 11A shows a progressive addition lens 10 which has a dioptric power matched to an eye 11, 11' of an observer 28, the dioptric power exactly correcting the eye 11, 11' of the observer 28 when looking through the near region zone 16 and the far region zone 20. Here, the astigmatism of the progressive addition lens 10 has the profile specified by the isoastigmatism lines 100. Here, the dioptric power does not comprise an additional astigmatism.

FIG. 11B shows the progressive addition lens 10 with a dioptric power component $K_1$, $K_3$ matched to the eye 11, 11' of the observer 28, the dioptric power component correcting the eye of the observer 28 when looking through the near region zone 16 and the far region zone 20 to the best possible extent, wherein a further dioptric power component $K_4$, namely an additional negative astigmatism with the cylindrical refractive power −0.25 DC and the axis location of $\varphi=0°$, has been superposed in the near region zone 16. This measure brings about an advantageous broadening of the near region zone 16, with, however, the extent of the far region zone 22 decreasing. Shown in FIG. 11C is the progressive addition lens 10 when, as a further dioptric power component $K_4$, the additional negative astigmatism with the cylindrical refractive power of −0.25 DC and the axis location of $\varphi=90°$ is superposed, in the near region zone 16, onto the dioptric power component $K_2$, matched to the eye 11, 11' of the observer 28, of the dioptric power which completely corrects the eye 11, 11' of the observer 28 when looking through the near region zone 16 and the far region zone 20. In relation to the progressive addition lens 10 shown in FIG. 11A, the far region zone 22 is broader in this case and the near region zone 16 is in turn slightly narrower.

In the progressive addition lens 10 shown in FIG. 11A, FIG. 11B, and FIG. 11C, the average dioptric fully corrective power is respectively constant in the region identified by the circular line 21.

Figure 11F:
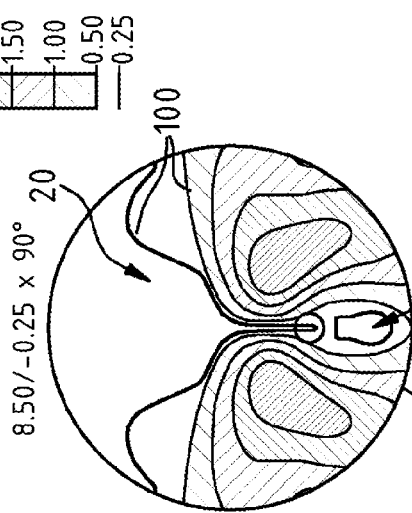
FIG. 11F shows yet another exemplary embodiment of a progressive addition lens.
Figure 11E:
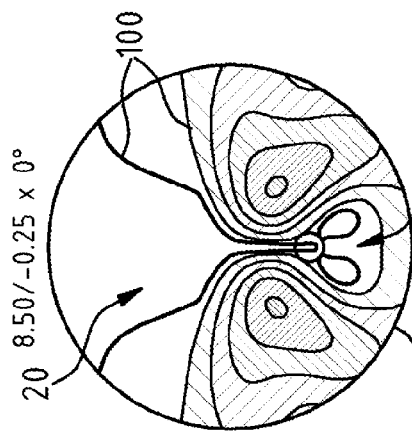
FIG. 11E shows another exemplary embodiment of a progressive addition lens.
Figure 11D:
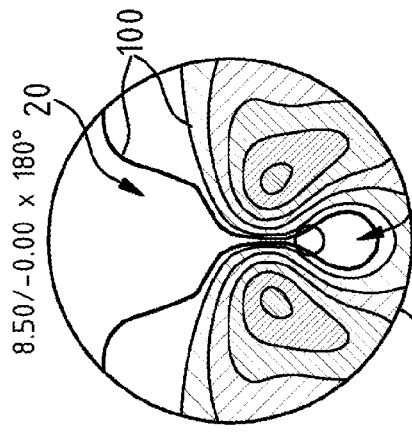
FIG. 11D shows a further exemplary embodiment a progressive addition lens.

In contrast thereto, the spherical power in the progressive addition lens 10 shown in FIG. 11D, FIG. 11E, and FIG. 11F is identical in the near region zone 16 and in the far region zone 20. In the progressive addition lens 10 in FIG. 11D, no additional astigmatism is superposed on the dioptric power component $K_2$, matched to an observer 28, of the dioptric power which corrects the eye of the observer 28 to the best possible extent when looking through the near region zone 16 and the far region zone 20.

FIG. 11E shows the progressive addition lens 10 with an additional negative astigmatism with the cylindrical refractive power −0.25 DC and the axis location $\varphi=0°$ superposed onto the dioptric power component $K_2$, matched to the observer 28, of the dioptric power as a further dioptric power component $K_4$.

FIG. 11F shows the progressive addition lens 10 with an additional negative astigmatism with the cylindrical refractive power −0.25 DC and the axis location $\varphi=90°$ superposed onto the dioptric power component $K_2$, matched to the observer 28, of the dioptric power as a further dioptric power component $K_4$.

FIG. 11E shows that, in the case of the additional negative astigmatism with the axis location of $\varphi=0°$, the distance between the isoastigmatism lines with the cylindrical refractive power of +0.5 DC and +1.00 DC is increased in relation to the progressive addition lens 10 from FIG. 11E. What emerges from FIG. 11F is that, in the case of the additional negative astigmatism with the axis location of $\varphi=90°$, the distance between the isoastigmatism lines with the cylindrical refractive power of +0.5 DC and +1.00 DC is reduced in relation to the progressive addition lens 10 from FIG. 11E.

Therefore, what emerges from FIGS. 11A to 11E is that a progressive addition lens with an additional negative astigmatism with the cylindrical refractive power of −0.25 DC and the axis location of $\varphi=0°$ for the vicinity and an additional negative astigmatism with the axis location of $\varphi=90°$ for the distance can bring about not only the observation of the object region with a correspondingly higher depth of field ST for the observer, but also that such a progressive addition lens also offers an improved visual comfort on account of the larger extent of the near region zone 16 and far region zone 20 in the case of the same profile of the spherical refractive power.

Moreover, it should be noted that a progressive addition lens 10, which has an above-described additional astigmatism in the near region zone 16 and far region zone 20, may also be embodied for an observer 28 with a progression between far-field reference point and near-field reference point and with a reduced spherical refractive power at the near-field reference point on account of the correspondingly increased depth of field. This measure also has a correspondingly larger extent of the near region zone 86 and of the far region zone 88 as a consequence.

To sum up, the following preferred features of the disclosure should be noted in particular:

The disclosure relates to the use of an optical visual aid 6 comprising at least one spectacle lens 10 by an observer 28 for looking at an object 15. Here, the optical visual aid 6 has a dioptric power matched to an eye 11, 11' of the observer 28 for at least one viewing direction A, B, the dioptric power being composed of a plurality of dioptric power components $K_1$, $K_2$, $K_3$, $K_4$. Here, a first dioptric power component $K_1$, $K_2$ of the plurality of dioptric power components $K_1$, $K_2$, $K_3$, $K_4$ has a best possible corrective power for the eye 11, 11' of the observer 28 at a defined distance $A_S$ of the object 15 from the corneal vertex of the eye 11, 11'. At the same time, a further dioptric power component $K_2$, $K_4$ of the plurality of dioptric power components $K_1$, $K_2$, $K_3$, $K_4$ has an additional astigmatic, partly corrective power for the viewing direction A, B for the eye 11, 11' of the observer 28 at the defined distance $A_S$. The disclosure also relates to a method for setting the parameterization of a visual aid 6 suitable for the specified use, and a system 26 for ascertaining the parameterization of such a visual aid 6.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

LIST OF REFERENCE SIGNS

A, B Viewing direction
6 Optical visual aid
7 Rim
8 Spectacle lens blank
9 Spectacle frame
10 Spectacle lens
11, 11' Eye
12 Spectacle lens front surface
14 Spectacle lens rear surface
15 Object
16 Near region zone
18 Near-field reference point
20 Far region zone
21 Circular line
22 Far-field reference point
24 Progression channel
26 System
28 Observer
30 Testing spectacles
31 Testing lens
32 Chin support
34 Visualization apparatus
36 Optotypes
38 OLED display
40 Rail
42 Computer unit
44 Stepper motor
45 Double-headed arrow
46 Optical lenses
47 Distance
48 Optical lenses
50 Graph
52 Curve
54, 54' Curve
56, 56' Curve
58, 58' Curve
60 Graph
62 Second system
64 Visualization apparatus
66 First display device
67 Display surface
68 Second display device
70 Handle
72 Position sensor
74 Position sensor
76 Position sensor
78 Pushbutton
80 Docking station
82 Camera
83 Accumulator
84 Insertion frame
86, 88 Graph
92 System
94 Measuring device
96 Retina
97 Laser light beam
98 Computer unit
100 Isoastigmatism line
102 Interface

What is claimed is:

1. An optical visual aid comprising:
at least one spectacle lens of an observer for looking at an object,
wherein the at least one spectacle lens of the optical visual aid has a dioptric power matched to an eye of the observer for at least one viewing direction (A, B), the dioptric power including a plurality of dioptric power components ($K_1$, $K_2$, $K_3$, $K_4$),
wherein a first dioptric power component ($K_1$, $K_3$) of the plurality of dioptric power components ($K_1$, $K_2$, $K_3$, $K_4$) has a first corrective power for the at least one viewing direction (A, B) of the eye of the observer at a defined distance $A_S$ of the object from a corneal vertex of the eye,
wherein a further dioptric power component ($K_2$, $K_4$) of the plurality of dioptric power components ($K_1$, $K_2$, $K_3$, $K_4$) has an additional astigmatic power for the at least one viewing direction of the eye of the observer at the defined distance $A_S$,
wherein the first corrective power of the first dioptric power component contributes to an overall dioptric power of the visual aid by bringing a refraction for correcting a refractive error of the observer to a maximum visual acuity of the observer, up to ⅕ D of a prescribed spherical power and up to ⅕ DC of a prescribed astigmatic power, and an axis location of ±5° of the prescribed astigmatic power in a TABO scheme,
wherein the additional astigmatic power for the at least one viewing direction (A, B) at the defined distance $A_S$ of the object reduces the visual acuity of the observer by no more than 0.2 log MAR in relation to the visual acuity obtained by the first dioptric power component, wherein the first dioptric power component ($K_1$) has a power which, for a distance $A_S \geq 4$ m of the object from the corneal vertex of the eye, corrects the eye of the observer for the at least one viewing direction (A), wherein the further dioptric power component ($K_2$) has an additional negative astigmatic power for the eye of the observer for the at least one viewing direction (A), and wherein the additional negative astigmatic power is a cylindrical refractive power BK with $-1.0$ DC$\leq$BK$\leq-0.125$ DC and with an axis location $\varphi$, specified in the TABO scheme, with $70° \leq \varphi \leq 110°$, or with an axis location $\varphi$, specified in the TABO scheme, with $-20° \leq \varphi \leq 20°$.

2. The optical visual aid as claimed in claim 1, wherein the dioptric power matched to the eye of the observer includes at least two first and two further dioptric power components, wherein one of the two first dioptric power components ($K_1$) has the power which, for a distance $A_S \leq 1$ m of the object from the corneal vertex of the eye, corrects the eye of the observer for a first viewing direction (B) and the other one of the two first dioptric power components ($K_3$) has the power which, for a distance $A_S \geq 4$ m of the object from the corneal vertex of the eye, corrects the eye of the observer for a further viewing direction, wherein one of the two second dioptric power components ($K_2$) has an additional negative astigmatic power for the eye of the observer with a cylindrical refractive power BK with $-1.0$ DC$\leq$BK$\leq-0.125$ DC and an axis location $\varphi$, specified in the TABO scheme, with $70° \leq \varphi \leq 110°$ for the viewing direction (B) or an axis location $\varphi$ with $-20° \leq \varphi \leq 20°$ for the viewing direction (B), and wherein the other one of the two second dioptric power components ($K_4$) has an additional negative astigmatic power for the eye of the observer with a cylindrical refractive power BK with $-1.0$ DC$\leq$BK$\leq-0.125$ DC and an axis location $\varphi$, specified in the TABO scheme, with $70° \leq \varphi \leq 110°$ or an axis location $\varphi$ with $-20° \leq \varphi \leq 20°$ for the further viewing direction (A).

3. The optical visual aid as claimed in claim 2, wherein the one of the two first dioptric power components ($K_1$) with the power which, for the distance $A_S \leq 1$ m, corrects the eye has a spherical refractive power SBK for the viewing direction (B) which has been reduced by a value $\Delta$SBK, with $-1.0$ D$\leq \Delta$SBK$\leq-0.1$ D, in relation to a power which, for a distance 25 cm$\leq A_S \leq 40$ cm of the object from the corneal vertex of the eye, corrects the eye of the observer.

4. An optical visual aid comprising:

at least one spectacle lens of an observer for looking at an object, wherein the at least one spectacle lens of the optical visual aid has a dioptric power matched to an eye of the observer for at least one viewing direction (A, B), the dioptric power including a plurality of dioptric power components ($K_1, K_2, K_3, K_4$), wherein a first dioptric power component ($K_1, K_3$) of the plurality of dioptric power components ($K_1, K_2, K_3, K_4$) has a first corrective power for the at least one viewing direction (A, B) of the eye of the observer at a defined distance $A_S$ of the object from a corneal vertex of the eye, wherein a further dioptric power component ($K_2, K_4$) of the plurality of dioptric power components ($K_1, K_2, K_3,$ $K_4$) has an additional astigmatic power for the at least one viewing direction of the eye of the observer at the defined distance $A_S$, wherein the first corrective power of the first dioptric power component contributes to an overall dioptric power of the visual aid by bringing a refraction for correcting a refractive error of the observer to a maximum visual acuity of the observer, up to ⅕ D of a prescribed spherical power and up to ⅕ DC of a prescribed astigmatic power, and an axis location of $\pm 5°$ of the prescribed astigmatic power in a TABO scheme, wherein the additional astigmatic power for the at least one viewing direction (A, B) reduces the visual acuity of the observer by no more than 0.2 log MAR in relation to the visual acuity obtained by the first dioptric power component, wherein the first dioptric power component ($K_3$) has the power which, for a distance $A_S \leq 1$ m of the object from the corneal vertex of the eye, corrects the eye of the observer for the at least one viewing direction, wherein the further dioptric power component ($K_4$) has an additional negative astigmatic power for the eye of the observer for the at least one viewing direction (B), and wherein the additional negative astigmatic power is a cylindrical refractive power BK with $-1.0$ DC$\leq$BK$\leq-0.125$ DC and with an axis location $\varphi$, specified in the TABO scheme, with $70° \leq \varphi \leq 110°$, or with an axis location $\varphi$, specified in the TABO scheme, with $-20° \leq \varphi \leq 20°$.

5. The optical visual aid as claimed in claim 4, wherein the first dioptric power component ($K_3$) has a spherical refractive power SBK for the viewing direction which has been reduced by the value $\Delta$SBK, with $-1.0$ D$\leq \Delta$SBK$\leq-0.1$ D, in relation to a power which, for a distance 25 cm$\leq A_S \leq 40$ cm of an object from the corneal vertex of the eye, corrects the eye of the observer.

6. The optical visual aid as claimed in claim 4, wherein the dioptric power matched to the eye of the observer includes at least two first and two further dioptric power components, wherein one of the two first dioptric power components ($K_1$) has the power which, for a distance $A_S \leq 1$ m of the object from the corneal vertex of the eye, corrects the eye of the observer for a first viewing direction (B) and the other one of the two first dioptric power components ($K_3$) has the power which, for a distance $A_S \geq 4$ m of the object from the corneal vertex of the eye, corrects the eye of the observer for a further viewing direction, wherein one of the two second dioptric power components ($K_2$) has an additional negative astigmatic power for the eye of the observer with a cylindrical refractive power BK with $-1.0$ DC$\leq$BK$\leq-0.125$ DC and an axis location $\varphi$, specified in the TABO scheme, with $70° \leq \varphi \leq 110°$ for the viewing direction (B) or an axis location $\varphi$ with $-20° \leq \varphi \leq 20°$ for the viewing direction (B), and wherein the other one of the two second dioptric power components ($K_4$) has an additional negative astigmatic power for the eye of the observer with a cylindrical refractive power BK with $-1.0$ DC$\leq$BK$\leq-0.125$ DC and an axis location $\varphi$, specified in the TABO scheme, with $70° \leq \varphi \leq 110°$ or an axis location $\varphi$ with $-20° \leq \varphi \leq 20°$ for the further viewing direction (A).

7. The optical visual aid as claimed in claim 6, wherein the one of the two first dioptric power components ($K_1$) with the power which, for the distance $A_S \leq 1$ m, corrects the eye has a spherical refractive power SBK for the viewing direction (B) which has been reduced by a value ΔSBK, with −1.0 D≤ΔSBK≤−0.1 D, in relation to a power which, for a distance 25 cm≤$A_S$≤40 cm of the object from the corneal vertex of the eye, corrects the eye of the observer.

8. A method for ascertaining a sought parameterization ($P_E$) of a dioptric power, including a plurality of dioptric power components ($K_1$, $K_2$, $K_3$, $K_4$), of an optical visual aid with at least one spectacle lens for an eye of an observer, performed by a computer program including program code when executed by a processor and being stored on a non-transitory computer-readable storage medium, the method comprising:
displaying optotypes on a display of an eyesight test device at a defined distance As from a corneal vertex of the eye of the observer for at least one viewing direction (A, B),
providing a prescription for an optical visual aid by determining a first parameterization ($P_A$) of the dioptric power of the optical visual aid in the form of a spherical power, an astigmatic power and an axis location thereof, as well as a prismatic power and a basis thereof, in accordance with a first power component ($K_1$, $K_2$), which has a corrective power, from a correction of the eye of the observer for the defined distance $A_S$,
correcting the determined first parameterization ($P_A$) by an additional further dioptric power component ($K_2$, $K_4$), which has an additional astigmatic power for the at least one viewing direction (A, B) at the defined distance $A_S$, thereby obtaining a corrected first parameterization ($P_A$)', and
setting the corrected first parameterization ($P_A$)' as the sought parameterization ($P_E$),
wherein the corrective power of the first parameterization ($P_A$)' of the dioptric power of the visual aid is a property that, for the at least one viewing direction (A, B), brings about a correction of the refractive error of the observer to a maximum visual acuity of the observer, up to ⅕ D of a prescribed spherical power and up to ⅕ DC of a prescribed astigmatic power and an axis location of ±5° of the prescribed astigmatic power in a TABO scheme,
wherein the additional astigmatic power for the at least one viewing direction (A, B) at the defined distance $A_S$ reduces a visual acuity of the observer by no more than 0.2 log MAR in relation to the maximum visual acuity of the observer obtained by the first dioptric power component,
wherein the correction for the eye of the observer for the at least one viewing direction (B) is a correction for a distance $A_S$≤1 m of an object from the corneal vertex of the eye and the additional further dioptric power component ($K_4$) has an additional negative astigmatic power for the eye of the observer,
wherein the additional negative astigmatic power is a cylindrical refractive power BK with −1.0 DC≤BK≤−0.125 DC and with an axis location φ, specified in the TABO scheme, with 70°≤φ≤110°, or an axis location φ with −20°≤φ≤20°, and
wherein the sought parameterization ($P_E$) increases a depth of field of the optical visual aid compared to the first parameterization ($P_A$).

9. The method as claimed in claim 8, wherein the determined first parameterization ($P_A$) is corrected by a dioptric power component with a spherical refractive power SBK which has been reduced by the value ΔSBK, with −1.0 D≤ΔSBK≤−0.1 D, in relation to a power which, for a distance 25 cm≤$A_S$≤40 cm of an object from the corneal vertex of the eye, corrects the eye for the maximum visual acuity of the observer.

10. The method as claimed in claim 8, wherein the correction for the eye of the observer additionally is a correction for a distance $A_S$≥4 m of an object from the corneal vertex of the eye for a further viewing direction (B), and the first parameterization ($P_A$) of the optical visual aid is also ascertained therefrom, and the first parameterization ($P_A$) ascertained thus is also corrected by an additional dioptric power component ($K_3$) and the corrected first parameterization ($P_A$)' is set as the sought parameterization ($P_E$), and
wherein the additional dioptric power component ($K_3$) for the eye of the observer is a negative astigmatic power with the cylindrical refractive power BK with −1.0 DC≤BK≤−0.125 DC and with an axis location φ, specified in the TABO scheme, with 70°≤φ≤110°, or with −20°≤φ≤20°.

11. A method for ascertaining a sought parameterization ($P_E$) of a dioptric power, including a plurality of dioptric power components ($K_1$, $K_2$, $K_3$, $K_4$), of an optical visual aid with at least one spectacle lens for an eye of an observer performed by a computer program including program code when executed by a processor and being stored on a non-transitory computer-readable storage medium, the method comprising:
displaying optotypes on a display of an eyesight test device at a defined distance As from a corneal vertex of the eye of the observer for at least one viewing direction (A, B);
providing a prescription for an optical visual aid by determining a first parameterization ($P_A$) of the dioptric power of the optical visual aid in the form of a spherical power, an astigmatic power and an axis location thereof, as well as a prismatic power and a basis thereof, in accordance with a first power component ($K_1$, $K_2$), which has a corrective power, from a correction of the eye of the observer for the defined distance $A_S$;
correcting the determined first parameterization ($P_A$) by an additional further dioptric power component ($K_2$, $K_4$), which has an additional astigmatic power for the at least one viewing direction (A, B) at the defined distance $A_S$, thereby obtaining a corrected first parameterization ($P_A$)'; and
setting the corrected first parameterization ($P_A$)' as the sought parameterization ($P_E$),
wherein the corrective power of the first parameterization ($P_A$) of the dioptric power of the visual aid is a property that, for the at least one viewing direction (A, B), brings about a correction of the refractive error of the observer to a maximum visual acuity of the observer, up to ⅕ D of a prescribed spherical power and up to ⅕ DC of a prescribed astigmatic power and an axis location of ±5° of the prescribed astigmatic power in a TABO scheme,
wherein the additional astigmatic power for the at least one viewing direction (A, B) at the defined distance $A_S$ reduces a visual acuity of the observer by no more than 0.2 log MAR in relation to the maximum visual acuity of the observer obtained by the first dioptric power component,
wherein the correction for the eye of the observer for the at least one viewing direction (A) is a correction for a distance $A_S$≥4 m of an object from the corneal vertex of the eye and the additional further dioptric power component ($K_3$) has an additional negative astigmatic power for the eye of the observer, wherein the additional negative astigmatic power is a cylindrical refractive power BK with −1.0 DC≤BK≤−0.125 DC and with an axis location φ, specified in the TABO scheme, with 70°≤φ≤110°, or with −20°≤φ≤20°, and wherein the sought parameterization ($P_E$) increases a depth of field of the optical visual aid compared to the first parameterization ($P_A$).

12. A method for manufacturing an optical visual aid, the method comprising:

ascertaining a sought parameterization ($P_E$) of a dioptric power, including a plurality of dioptric power components ($K_1$, $K_2$, $K_3$, $K_4$), of an optical visual aid with at least one spectacle lens for an eye of an observer, determining a first parameterization ($P_A$) of the dioptric power of the optical visual aid in the form of a spherical power, an astigmatic power and an axis location thereof, as well as a prismatic power and a basis thereof, in accordance with a first power component ($K_1$, $K_2$), which has a corrective power, from a correction of the eye of the observer for at least one defined distance $A_S$ of an object from a corneal vertex of the eye for at least one viewing direction (A, B), correcting the determined first parameterization ($P_A$) by an additional further dioptric power component ($K_2$, $K_4$), which has an additional astigmatic power for the at least one viewing direction (A, B) at the defined distance $A_S$, thereby obtaining a corrected first parameterization ($P_A$)', setting the corrected first parameterization ($P_A$)' as the sought parameterization ($P_E$), and manufacturing the optical visual aid based on a prescription for spectacles including the sought parameterization ($P_E$), wherein the corrective power of the corrected first parameterization ($P_A$)' of the dioptric power of the visual aid is a property that, for the at least one viewing direction (A, B), brings about a correction of the refractive error of the observer to a maximum visual acuity of the observer, up to ⅕ D of a prescribed spherical power and up to ⅕ DC of a prescribed astigmatic power and an axis location of ±5° of the prescribed astigmatic power in a TABO scheme, wherein the additional astigmatic power for the at least one viewing direction (A, B) at the defined distance $A_S$ reduces a visual acuity of the observer by no more than 0.2 log MAR in relation to the maximum visual acuity of the observer obtained by the first dioptric power component, wherein the correction for the eye of the observer for the at least one viewing direction (B) is a correction for a distance $A_S$≤1 m of an object from the corneal vertex of the eye and the additional further dioptric power component ($K_4$) has an additional negative astigmatic power for the eye of the observer, and wherein the additional negative astigmatic power is a cylindrical refractive power BK with −1.0 DC≤BK≤−0.125 DC and with an axis location φ, specified in the TABO scheme, with 70°≤φ≤110°, or an axis location φ with −20°≤φ≤20°.

13. A method for manufacturing an optical visual aid, the method comprising:

ascertaining a sought parameterization ($P_E$) of a dioptric power, including a plurality of dioptric power components ($K_1$, $K_2$, $K_3$, $K_4$), of an optical visual aid with at least one spectacle lens for an eye of an observer, determining a first parameterization ($P_A$) of the dioptric power of the optical visual aid in the form of a spherical power, an astigmatic power and an axis location thereof, as well as a prismatic power and a basis thereof, in accordance with a first power component ($K_1$, $K_2$), which has a corrective power, from a correction of the eye of the observer for at least one defined distance $A_S$ of an object from a corneal vertex of the eye for at least one viewing direction (A, B), correcting the determined first parameterization ($P_A$) by an additional further dioptric power component ($K_2$, $K_4$), which has an additional astigmatic power for the at least one viewing direction (A, B) at the defined distance $A_S$, thereby obtaining a corrected first parameterization ($P_A$)', setting the corrected first parameterization ($P_A$)' as the sought parameterization ($P_E$), and manufacturing the optical visual aid based on a prescription for spectacles including the sought parameterization ($P_E$), wherein the corrective power of the corrected first parameterization ($P_A$)' of the dioptric power of the visual aid is a property that, for the at least one viewing direction (A, B), brings about a correction of the refractive error of the observer to a maximum visual acuity of the observer, up to ⅕ D of a prescribed spherical power and up to ⅕ DC of a prescribed astigmatic power and an axis location of ±5° of the prescribed astigmatic power in a TABO scheme, wherein the additional astigmatic power for the at least one viewing direction (A, B) at the defined distance $A_S$ reduces a visual acuity of the observer by no more than 0.2 log MAR in relation to the maximum visual acuity of the observer obtained by the first dioptric power component, wherein the correction for the eye of the observer for the at least one viewing direction (A) is a correction for a distance $A_S$≥4 m of an object from the corneal vertex of the eye and the additional further dioptric power component ($K_3$) has an additional negative astigmatic power for the eye of the observer, and wherein the additional negative astigmatic power is a cylindrical refractive power BK with −1.0 DC≤BK≤−0.125 DC and with an axis location φ, specified in the TABO scheme, with 70°≤φ≤110°, or an axis location φ with −20°≤φ≤20°.

14. A method of calculating a dioptric power of an optical visual aid with at least one spectacle lens for an eye of an observer performed by a computer program including program code when executed by a processor and being stored on a non-transitory computer-readable storage medium, the method comprising:

displaying optotypes on a display of an eyesight test device at a defined distance As from a corneal vertex of the eye of the observer for at least one viewing direction (A, B), ascertaining a sought parameterization ($P_E$) of a dioptric power, including a plurality of dioptric power components ($K_1$, $K_2$, $K_3$, $K_4$), of an optical visual aid with at least one spectacle lens for the eye of the observer, determining a first parameterization ($P_A$) of the dioptric power of the optical visual aid in the form of a spherical power, an astigmatic power and an axis location thereof, as well as a prismatic power and a basis thereof, in accordance with a first power component ($K_1$, $K_2$), which has a corrective power, from a correction of the eye of the observer for the defined distance $A_S$, correcting the determined first parameterization ($P_A$) by an additional further dioptric power component ($K_2$, $K_4$), which has an additional astigmatic power for the at least one viewing direction (A, B) at the defined distance $A_S$, thereby obtaining a corrected first parameterization ($P_A$)', setting the corrected first parameterization ($P_A$)' as the sought parameterization ($P_E$), and calculating the optical power for the optical visual aid based on the sought parameterization ($P_E$), the optical visual aid having an increased depth of field compared to an optical visual aid with a prescription based on the first parameterization ($P_A$), wherein the corrective power of the corrected first parameterization ($P_A$)' of the dioptric power of the visual aid is a property that, for the at least one viewing direction (A, B), brings about a correction of the refractive error of the observer to a maximum visual acuity of the observer, up to ⅛ D of a prescribed spherical power and up to ⅛ DC of a prescribed astigmatic power and an axis location of ±5° of the prescribed astigmatic power in a TABO scheme, wherein the additional astigmatic power for the at least one viewing direction (A, B) at the defined distance $A_S$ reduces a visual acuity of the observer by no more than 0.2 log MAR in relation to the maximum visual acuity of the observer obtained by the first dioptric power component, wherein the correction for the eye of the observer for the at least one viewing direction (B) is a correction for a distance $A_S \le 1$ m of an object from the corneal vertex of the eye and the additional further dioptric power component ($K_4$) has an additional negative astigmatic power for the eye of the observer, and wherein the additional negative astigmatic power is a cylindrical refractive power BK with $-1.0$ DC$\le$BK$\le-0.125$ DC and with an axis location φ, specified in the TABO scheme, with 70°$\le$φ$\le$110°, or an axis location φ with $-20°\le$φ$\le 20°$.

15. A method of calculating a dioptric power of an optical visual aid with at least one spectacle lens for an eye of an observer performed by a computer program including program code when executed by a processor and being stored on a non-transitory computer-readable storage medium, the method comprising:

displaying optotypes on a display of an eyesight test device at a defined distance As from a corneal vertex of the eye of the observer for at least one viewing direction (A, B), ascertaining a sought parameterization ($P_E$) of a dioptric power, including a plurality of dioptric power components ($K_1$, $K_2$, $K_3$, $K_4$), of an optical visual aid with at least one spectacle lens for the eye of the observer, determining a first parameterization ($P_A$) of the dioptric power of the optical visual aid in the form of a spherical power, an astigmatic power and an axis location thereof, as well as a prismatic power and a basis thereof, in accordance with a first power component ($K_1$, $K_2$), which has a corrective power, from a correction of the eye of the observer for the defined distance $A_S$, correcting the determined first parameterization ($P_A$) by an additional further dioptric power component ($K_2$, $K_4$), which has an additional astigmatic power for the at least one viewing direction (A, B) at the defined distance $A_S$, thereby obtaining a corrected first parameterization ($P_A$)' setting the corrected first parameterization ($P_A$)' as the sought parameterization ($P_E$), and calculating the optical power for the optical visual aid based on the sought parameterization ($P_E$), the optical visual aid having an increased depth of field compared to an optical visual aid with a prescription based on the first parameterization ($P_A$), wherein the corrective power of the corrected first parameterization ($P_A$)' of the dioptric power of the visual aid is a property that, for the at least one viewing direction (A, B), brings about a correction of the refractive error of the observer to a maximum visual acuity of the observer, up to ⅛ D of a prescribed spherical power and up to ⅛ DC of a prescribed astigmatic power and an axis location of ±5° of the prescribed astigmatic power in a TABO scheme, wherein the additional astigmatic power for the at least one viewing direction (A, B) at the defined distance $A_S$ reduces a visual acuity of the observer by no more than 0.2 log MAR in relation to the maximum visual acuity of the observer obtained by the first dioptric power component, wherein the correction for the eye of the observer for the at least one viewing direction (A) is a correction for a distance $A_S \ge 4$ m of an object from the corneal vertex of the eye and the additional further dioptric power component ($K_3$) has an additional negative astigmatic power for the eye of the observer, and wherein the additional negative astigmatic power is a cylindrical refractive power BK with $-1.0$ DC$\le$BK$\le-0.125$ DC and with an axis location φ, specified in the TABO scheme, with 70°$\le$φ$\le$110°, or an axis location φ with $-20°\le$φ$\le 20°$.

16. A method of providing an optical visual aid to an observer, the method comprising:

displaying optotypes on a display of an eyesight test device at a defined distance As from a corneal vertex of the eye of the observer for at least one viewing direction (A, B), ascertaining a sought parameterization ($P_E$) of a dioptric power, including a plurality of dioptric power components ($K_1$, $K_2$, $K_3$, $K_4$), of an optical visual aid with at least one spectacle lens for the eye of the observer, determining a first parameterization ($P_A$) of the dioptric power of the optical visual aid in the form of a spherical power, an astigmatic power and an axis location thereof, as well as a prismatic power and a basis thereof, in accordance with a first power component ($K_1$, $K_2$), which has a corrective power, from a correction of the eye of the observer for the defined distance $A_S$, correcting the determined first parameterization ($P_A$) by an additional further dioptric power component ($K_2$, $K_4$), which has an additional astigmatic power for the at least one viewing direction (A, B) at the defined distance $A_S$, thereby obtaining a corrected first parameterization ($P_A$)', setting the corrected first parameterization ($P_A$)' as the sought parameterization ($P_E$), and selecting a spectacle lens having the sought parameterization ($P_E$) for the optical visual aid from a stock of spectacle lenses present in virtual or physical form, the optical visual aid having an increased depth of field compared to an optical visual aid with a prescription based on the first parameterization ($P_A$), wherein the corrective power of the corrected first parameterization ($P_A$)' of the dioptric power of the visual aid is a property that, for the at least one viewing direction (A, B), brings about a correction of the refractive error of the observer to a maximum visual acuity of the observer, up to ⅓ D of a prescribed spherical power and up to ⅓ DC of a prescribed astigmatic power and an axis location of ±5° of the prescribed astigmatic power in a TABO scheme, wherein the additional astigmatic power for the at least one viewing direction (A, B) at the defined distance $A_S$ reduces a visual acuity of the observer by no more than 0.2 log MAR in relation to the maximum visual acuity of the observer obtained by the first dioptric power component, wherein the correction for the eye of the observer for the at least one viewing direction (B) is a correction for a distance $A_S \leq 1$ m of an object from the corneal vertex of the eye and the additional further dioptric power component ($K_4$) has an additional negative astigmatic power for the eye of the observer, wherein the additional negative astigmatic power is a cylindrical refractive power BK with $-1.0$ DC$\leq$BK$\leq-0.125$ DC and with an axis location $\varphi$, specified in the TABO scheme, with 70°$\leq\varphi\leq$110°, or an axis location $\varphi$ with $-20°\leq\varphi\leq 20°$; and providing the optical visual aid to the observer.

17. A method of providing an optical visual aid to an observer, the method comprising:

displaying optotypes on a display of an eyesight test device at a defined distance As from a corneal vertex of the eye of the observer for at least one viewing direction (A, B), ascertaining a sought parameterization ($P_E$) of a dioptric power, including a plurality of dioptric power components ($K_1$, $K_2$, $K_3$, $K_4$), of an optical visual aid with at least one spectacle lens for the eye of the observer, determining a first parameterization ($P_A$) of the dioptric power of the optical visual aid in the form of a spherical power, an astigmatic power and an axis location thereof, as well as a prismatic power and a basis thereof, in accordance with a first power component ($K_1$, $K_2$), which has a corrective power, from a correction of the eye of the observer for the defined distance $A_S$, correcting the determined first parameterization ($P_A$) by an additional further dioptric power component ($K_2$, $K_4$), which has an additional astigmatic power for the at least one viewing direction (A, B) at the defined distance $A_S$, thereby obtaining a corrected first parameterization ($P_A$)', setting the corrected first parameterization ($P_A$)' as the sought parameterization ($P_E$), and selecting a spectacle lens having the sought parameterization ($P_E$) for the optical visual aid from a stock of spectacle lenses present in virtual or physical form, the optical visual aid having an increased depth of field compared to an optical visual aid with a prescription based on the first parameterization ($P_A$), wherein the corrective power of the first parameterization ($P_A$)' of the dioptric power of the visual aid is a property that, for the at least one viewing direction (A, B), brings about a correction of the refractive error of the observer to a maximum visual acuity of the observer, up to ⅓ D of a prescribed spherical power and up to ⅓ DC of a prescribed astigmatic power and an axis location of ±5° of the prescribed astigmatic power in a TABO scheme, wherein the additional astigmatic power for the at least one viewing direction (A, B) at the defined distance $A_S$ reduces a visual acuity of the observer by no more than 0.2 log MAR in relation to the maximum visual acuity of the observer obtained by the first dioptric power component, wherein the correction for the eye of the observer for the at least one viewing direction (A) is a correction for a distance $A_S \geq 4$ m of an object from the corneal vertex of the eye and the additional further dioptric power component ($K_3$) has an additional negative astigmatic power for the eye of the observer, wherein the additional negative astigmatic power is a cylindrical refractive power BK with $-1.0$ DC$\leq$BK$\leq-0.125$ DC and with an axis location $\varphi$, specified in the TABO scheme, with 70°$\leq\varphi\leq$110°, or an axis location $\varphi$ with $-20°\leq\varphi\leq 20°$, and providing the visual aid to the observer.

* * * * *